(12) United States Patent
Tabor et al.

(10) Patent No.: US 9,732,026 B2
(45) Date of Patent: Aug. 15, 2017

(54) REACTION PRODUCTS CONTAINING HYDROXYALKYLTEREPHTHALATES AND METHODS OF MAKING AND USING SAME

(71) Applicant: Resinate Technologies, Inc., Plymouth, MI (US)

(72) Inventors: Rick Tabor, Plymouth, MI (US); Daniel James Seyer, Ballwin, MO (US); Kristopher M Felice, Wolverine Lake, MI (US); Adam W Emerson, Ypsilanti, MI (US); Matthew Thomas Brown, Novi, MI (US); Kyle Harris McGrath, Plymouth, MI (US); Mickey Kellerman, Chicago, IL (US); Kevin Anthony Rogers, Farmington, MI (US); Jack Rogers Kovsky, Livonia, MI (US); Matthew James Beatty, Ann Arbor, MI (US); Eric David Vrabel, Ferndale, MI (US)

(73) Assignee: Resinate Technologies, Inc., Plymouth, MI (US)

( * ) Notice: Subject to any disclaimer, the term of this patent is extended or adjusted under 35 U.S.C. 154(b) by 0 days.

(21) Appl. No.: 14/650,614

(22) PCT Filed: Dec. 17, 2013

(86) PCT No.: PCT/US2013/075517
§ 371 (c)(1),
(2) Date: Jun. 9, 2015

(87) PCT Pub. No.: WO2014/093995
PCT Pub. Date: Jun. 19, 2014

(65) Prior Publication Data
US 2015/0315325 A1 Nov. 5, 2015

Related U.S. Application Data

(63) Continuation-in-part of application No. PCT/US2013/075510, filed on Dec. 16, 2013.
(Continued)

(51) Int. Cl.
| | |
|---|---|
| *C08G 18/08* | (2006.01) |
| *C08G 18/28* | (2006.01) |
| *B22F 1/00* | (2006.01) |
| *C08G 61/04* | (2006.01) |
| *C07C 67/03* | (2006.01) |
| *C08F 283/00* | (2006.01) |
| *C07C 67/54* | (2006.01) |

(Continued)

(52) U.S. Cl.
CPC ............ *C07C 67/03* (2013.01); *C07C 67/54* (2013.01); *C08F 283/006* (2013.01); *C08F 283/02* (2013.01); *C08G 18/0823* (2013.01); *C08G 18/222* (2013.01); *C08G 18/246* (2013.01); *C08G 18/341* (2013.01); *C08G 18/4202* (2013.01); *C08G 18/4225* (2013.01); *C08G 18/4288* (2013.01); *C08G 18/4833* (2013.01); *C08G 18/6659* (2013.01); *C08G 18/673* (2013.01); *C08G 18/755* (2013.01); *C08G 18/7621* (2013.01); *C09D 175/06* (2013.01); *C09D 175/16* (2013.01)

(58) Field of Classification Search
CPC ...... C08F 283/006; C07C 67/54; C07C 67/03; C09D 151/08
USPC .................................. 524/590, 589, 1; 520/1
See application file for complete search history.

(56) References Cited

U.S. PATENT DOCUMENTS

| | | | |
|---|---|---|---|
| 3,377,519 A | 4/1968 | Strong | |
| 3,412,054 A | 11/1968 | Milligan et al. | |

(Continued)

FOREIGN PATENT DOCUMENTS

| | | |
|---|---|---|
| EP | 2094756 A2 | 9/2009 |
| GB | 610136 | 10/1948 |

OTHER PUBLICATIONS

Supplementary European Search Report issued in EP Application No. 13862619.7 on Sep. 14, 2016.
(Continued)

*Primary Examiner* — Jessica E Whiteley
(74) *Attorney, Agent, or Firm* — Dilworth IP LLC

(57) ABSTRACT

The presently disclosed and/or claimed inventive concept(s) relates generally to oligomeric reaction products formed by the depolymerization of polyethylene terephthalate polymers and methods thereof. More specifically, the presently disclosed and/or claimed inventive concept(s) relates to oligomeric reaction products formed by the depolymerization of polyethylene terephthalate polymer obtained from, for example but not by way of limitation, waste products, such as beverage containers made from polyethylene terephthalate (PET). The oligomeric reaction products can, in one embodiment, be used as a starting material for polyurethanes. The presently disclosed and/or claimed inventive concept(s) also relates to processes for producing oligomeric reaction products from the depolymerization of polyethylene terephthalate. More particularly, the presently disclosed and/or claimed inventive concept(s) relates to a process of producing oligomeric reaction products of polyethylene terephthalate capable of controlling the removal of byproducts during the reaction. The presently disclosed and/or claimed inventive concept(s) also relates to ultraviolet curable urethane acrylate and polyethylene terephthalate compositions and methods of making and uses thereof.

13 Claims, 18 Drawing Sheets

Related U.S. Application Data

(60) Provisional application No. 61/737,485, filed on Dec. 14, 2012, provisional application No. 61/891,689, filed on Oct. 16, 2013.

(51) Int. Cl.

| | | |
|---|---|---|
| *C08F 283/02* | (2006.01) | |
| *C08G 18/48* | (2006.01) | |
| *C08G 18/66* | (2006.01) | |
| *C08G 18/67* | (2006.01) | |
| *C08G 18/75* | (2006.01) | |
| *C08G 18/76* | (2006.01) | |
| *C08G 18/22* | (2006.01) | |
| *C08G 18/24* | (2006.01) | |
| *C09D 175/06* | (2006.01) | |
| *C09D 175/16* | (2006.01) | |
| *C08G 18/34* | (2006.01) | |
| *C08G 18/42* | (2006.01) | |

(56) References Cited

U.S. PATENT DOCUMENTS

| | | | |
|---|---|---|---|
| 3,544,622 A | | 12/1970 | England |
| 3,801,273 A | | 4/1974 | Mays |
| 3,905,929 A | | 9/1975 | Noll |
| 3,920,598 A | | 11/1975 | Reiff et al. |
| 3,956,088 A | | 5/1976 | Fasell et al. |
| 4,609,680 A | | 9/1986 | Fujita et al. |
| 5,045,122 A | | 9/1991 | Tindall et al. |
| 5,223,544 A | | 6/1993 | Burkett et al. |
| 5,328,982 A | | 7/1994 | Tindall et al. |
| 5,414,107 A | | 5/1995 | Smith |
| 5,532,404 A | | 7/1996 | Gallagher |
| 5,559,159 A | | 9/1996 | Sublett et al. |
| 5,635,584 A | | 6/1997 | Ekart et al. |
| 5,710,315 A | | 1/1998 | Gallagher |
| 5,935,508 A | * | 8/1999 | Fernyhough ............ B29B 9/14 264/136 |
| 6,075,163 A | | 6/2000 | Roh et al. |
| 6,127,436 A | * | 10/2000 | Chatterjee ............ C08G 63/20 521/48.5 |
| 6,231,926 B1 | | 5/2001 | Ronzani et al. |
| 6,255,547 B1 | | 7/2001 | Smuda |
| 6,580,005 B1 | | 6/2003 | Yazaki et al. |
| 6,649,792 B2 | | 11/2003 | Sirek et al. |
| 6,723,873 B1 | | 4/2004 | Murdoch |
| 6,770,680 B2 | | 8/2004 | Klenk |
| 7,098,299 B1 | | 8/2006 | Gutierrez et al. |
| 7,173,150 B2 | | 2/2007 | Yazaki et al. |
| 7,338,981 B2 | | 3/2008 | Gutierrez et al. |
| 7,345,110 B2 | | 3/2008 | Gertzmann et al. |
| 2005/0096482 A1 | | 5/2005 | Tamada et al. |
| 2008/0102394 A1 | | 5/2008 | Pang et al. |
| 2009/0318579 A1 | | 12/2009 | Ikenaga |
| 2012/0259061 A1 | * | 10/2012 | Felice ............ C08G 18/6659 524/591 |

OTHER PUBLICATIONS

Chemical Recycling of Poly(ethylene teephthalate), Karayannidis, George P., Feb. 2, 2007; Macromolecular Materials and Engineering, Wiley Online Library, 35 pages.

International Search Report mailed in International Application No. PCT/US2013/075517on Apr. 15, 2014.

* cited by examiner

REACTION PRODUCTS CONTAINING HYDROXYALKYLTEREPHTHALATES AND METHODS OF MAKING AND USING SAME

CROSS REFERENCE TO RELATED APPLICATIONS/INCORPORATION BY REFERENCE STATEMENT

This application claims priority to U.S. Application Ser. No. 61/737,485, fled on Dec. 14, 2012; U.S. Application No. 61/891,689, filed on Oct. 16, 2013; and International Application No. PCT/US2013/075510, the entire contents of which are incorporated herein by reference in their entirety.

BACKGROUND

1. Field of the Inventive Concept(s)

The presently disclosed and/or claimed inventive concept(s) relates generally to oligomeric reaction products formed by the depolymerization of polyethylene terephthalate polymers and methods thereof. More specifically, the presently disclosed and/or claimed inventive concept(s) relates to oligomeric reaction products formed by the depolymerization of polyethylene terephthalate polymer obtained from, for example but not by way of limitation, waste products, such as beverage containers made from polyethylene terephthalate (PET). The oligomeric reaction products can, in one embodiment, be used as a starting material for polyurethanes. The presently disclosed and/or claimed inventive concept(s) also relates to processes for producing oligomeric reaction products from the depolymerization of polyethylene terephthalate. More particularly, the presently disclosed and/or claimed inventive concept(s) relates to a process of producing oligomeric reaction products of polyethylene terephthalate capable of controlling the removal of byproducts during the reaction. The presently disclosed and/or claimed inventive concept(s) also relates to ultraviolet curable urethane acrylate and polyethylene terephthalate compositions and methods of making and uses thereof.

2. Background of the Inventive Concept(s)

Plastics currently represent an ever-increasing portion of the mass of municipal solid waste in North American landfills. The conventional opinion regarding the resistance of plastics to degradation has positioned synthetic polymers as threats to the environment. Traditionally, such an environmental predisposition against synthetic polymers has pushed public opinion and lawmaking bodies to reduce their use and application. Although conservation efforts encourage consumers to use synthetic polymers (or products made front synthetic polymers) sparingly, such efforts will never completely eliminate their use in products. As such, landfills have become de facto repositories of high value petroleum products. Considerable energy, technology, and expense were invested into the production of these petroleum products and the disposal of them into landfills (and/or the biodegradation or incineration of the petroleum products) destroys all the value added efforts undertaken to create them.

In order to overcome the destruction of at least a part of the value added to these petroleum products, recycling has been encouraged. Recycling efforts can generally be divided into two types: mechanical and chemical recycling. Mechanical recycling promotes physical operations for washing and size reduction (for separating unwanted materials), and for reprocessing the recycled materials into new products. Although chemical treatments may be used in an effort to enhance the physical properties of the final product, mechanical recycling is mainly a physical process. Chemical recycling entails the use of chemical reactions to break the bonds of polymeric materials into lower molecular weight products ranging from monomers to intermediate oligomeric compounds. Commercial chemical recycling processes convert this plastic waste stream into an important commodity that can be placed within raw material markets.

Polyethylene terephthalate (PET), illustrated in FIG. 1, is a polymer belonging to the generic family of polyesters. PET is typically prepared by the condensation of terephthalic acid (TPA) and ethylene glycol (EG). TPA and EG are routinely derived from oil feedstock. PET is one of the most commonly recycled polymeric materials. In 1995, for example, $3.5 \times 10^4$ tons of PET were recycled in Europe. When pure TPA and EG are heated together they form the reactive monomer bis(hydroxyethyl) terephthalate ('BHET') along with a mixture of low molecular weight oligomers. This mélange of small chain products is permitted to further react and excess EG is removed to form high molecular weight PET, as illustrated in FIG. 2. Many companies produce virgin PET globally giving it different trade names. For example, some of the common trade names of commercially available PET include: RYNITE®, MYLAR®, and DACRON® (Du Pont de Nemours and Company Corporation, Wilmington, Del.) and EASTAPAK® (Eastman Chemical Company, Kingsport, Tenn.).

Academic and industrial studies have focused on chemically recycling PET into its monomeric roots of TPA and EG. Such efforts are often complicated by the high energy and extensive effort needed to purify the monomers from the reaction mixture. As such, chemical recycling of PET typically exhausts the advantages of using such a scrap or waste material. Exemplary methods of obtaining monomers of TPA and EG from PET are given in U.S. Pat. Nos. 3,377,519, 3,801,273, and 3,956,088, all of which are hereby incorporated by reference in their entirety. Similarly, U.S. Pat. No. 3,544,622 (the entire contents of which is hereby incorporated by reference) discloses a variation to previously known approaches wherein the reaction is carried out under conditions to produce a water insoluble salt of terephthalic acid which is separated, washed, and thereafter acidified to produce terephthalic acid. Additional patents have also been issued on various improvements to the above-noted processes, such as U.S. Pat. Nos. 5,045,122, 5,223,544, 5,328,982, 5,414,107, 5,532,404, 5,710,315, 6,075,163, 6,255,547, 6,580,005, 6,649,792, 6,723,873, 6,770,680, 7,098,299, 7,173,150, and 7,338,981, the entire contents of each of which are incorporated herein by reference in their entirety.

Popular pathways for chemical recycling of PET include: hydrolysis, methanolysis, and glycolysis, which are generically depicted in FIG. 3. In FIG. 3, 310 represents a generic polyethylene terephthalate chain of typical size with R1 being a non-hydrogen molecule; 320 represents a nucleophile intended to serve as a model molecule that can attack the ester carbonyl freely (identified as a strong nucleophile in this example as it would bear a charge), which can be generic in structure or species and may or may not be organic in nature, and wherein R2 can be hydrogenic (for hydrolysis), methyl (for methanolysis), or ethyl hydroxyl (for glycolysis); 330 represents the quaternary transition state after the nucleophile has attacked the carbonyl carbon and before the leaving group departs; 340 represents the new ester formed after the leaving group departs; and 350 represents the leaving group. These pathways all utilize transesterification to drive the depolymerization of PET. The extent of the depolymerization generally determines the value of the products formed. Interest in hydrolysis, for example, stems from its ability to provide a direct route to TPA and EG. Unfortunately, hydrolysis suffers from long reaction times at higher reaction temperatures and pressures as well as high costs associated with the purification and separation of the recycled TPA and EG. Hydrolysis of PET can be carried out in basic, acidic, or neutral conditions. Acidic and basic conditions promote an ester carbonyl attack that results in transesterification and the replacement of the organic alkoxide with a hydroxide. Neutral hydrolysis can be performed with a variety of well-studied Lewis acid metal cations, for example.

Methanolysis processes depolymerize PET with methanol at high temperature and pressure. The reaction products of PET methanolysis are dimethyl terephthalate (DMT) and EG, which can then be used as the raw materials to produce PET polymer. Methanolysis employs soluble catalysts (e.g., zinc acetate, magnesium acetate, cobalt acetate, etc.) to improve the reaction rate. As the polymer is broken into more simplified components, ethylene glycol is released. Recombination will rapidly begin if the catalyst, methanol, and DMT are not separated. DMT is typically obtained as a post reaction precipitate after cooling. The driving feature for methanolysis is the insertion of an alkoxide into the ester via transesterification.

Glycolysis promotes the depolymerization of PET using organic dialcohols along with transesterification catalysts to break the ester linkages and replace them with hydroxyl terminals. Preferred agents for such depolymerization are EG, diethylene glycol (DEG), and propylene glycol (PG). Such glycolysis agents can be recycled ethylene glycol, recycled diethylene glycol, and recycled propylene glycol, recycled neopentyl glycol, and combinations thereof. Glycolysis is conducted in a wide range of temperatures (e.g., 150-250° C.) and for a reaction period of from 0.5-8 hours. Usually, 0.5-2% by weight of catalyst (e.g., zinc acetate) in relation to the PET content is added.

The prior art generally teaches the depolymerization of PET by glycolysis in which the PET is depolymerized all the way to, almost exclusively, bis(hydroxyethyl) terephthalate (BHET), which requires an enormous amount of energy. See, e.g., U.S. Pat. Nos. 4,609,680, 5,559,159, and 5,635,584, British Pat. No. 610,136, and Japanese Pat. Pub. No. 61447/1973, the entire contents of each of which are incorporated by reference in their entirety. Additionally, such methods taught in the prior art have significant process limitations resulting from the unwanted solidification of reactants during the reaction processes (which interferes with the agitation of the system) and the formation of unwanted byproducts (which significantly interfere with the critical reaction temperature). Of particular significance is the formation of byproducts, which are generally produced by the glycol(s) reacting with itself and/or the catalyst(s). In one embodiment, the presently disclosed and/or claimed inventive concept(s) is directed to a process for depolymerizing PET into a blend of oligomers rather than a majority of BHET, which greatly reduces the energy necessary for recycling PET. Additionally, in another embodiment, the presently disclosed and/or claimed inventive concept(s) is directed to a process capable of controlling the removal of byproducts and other impurities formed during the depolymerization of PET, which shortens the reaction time while ensuring that the depolymerization reaction goes to completion and that the blend of oligomers produced are of a suitable product quality.

When constructing polymers, polyols are often used to enhance structural behavior and performance. Polyols are compounds with multiple hydroxyl groups available as nucleophiles for chemical reactions. Polyols can take on several shapes and sizes. From small molecules (e.g., glycerin) to larger and more complex molecules (e.g., sucrose). Polyols are primarily used as the starting point for many polymeric systems. Additionally, they can be reacted with propylene or ethylene oxide, for example, and made into polymers or large oligomers themselves. Such "self-made" polymers can thereafter be further reacted and/or combined with a wide variety of reactive moieties to form polymers of increasing complexity or specificity. In addition to being classified as either a polyether or a polyester, polyols can be further delineated according to their structure/application as either flexible or rigid. Such physical characteristics come from the particular polyol's functional moieties and molecular weight. Holding all else equal, flexible (SOFT) polyols have molecular weights from 2,000 to 10,000, and rigid (HARD) polyols have molecular weights from 250 to 700.

Conventional polyester polyols are rooted in virgin raw materials and manufacture products through replicate esterification of diacids and glycols (e.g., succinic acid and 1,2-propanediol). These polyester polyols are easily distinguished by the structure of the monomers, molecular weight, and steric hindrance. Other polyester polyols originate from reclaimed starting materials and, thereby, produce low molecular weight aromatic polyester polyols that retain enough utility to be carried forward into other polymeric systems. Occasionally, polyols are blends of two or more polyols, each of specific molecular weights, to thereby provide intermediate molecular weight materials.

Polyols can be made, for example, by reacting epoxides (e.g., ethylene oxide) with an initiating molecule or agent, such as water. Such a process can efficiently make polyether diols like polyethylene glycol, polypropylene glycol, and poly(tetramethylene ether) glycol. Polyether polyols account for about 90% of the polymeric polyols used industrially with the remaining 10% being polyester polyols.

When polyols are reacted with a highly reactive polyisocyanate, a polyurethane is produced. Polyurethanes are used to make many things including, for example but without limitation, automotive seats, elastomeric shoe soles, fibers (e.g., SPANDEX®, Invista S.a.r.l., Wichita, Kans.), adhesives, and foams used in, for example, insulation panels, seals, and gaskets.

Polyurethane (PU) polymers, since their inception, have proven to be diverse in structure and function. The production of polyurethanes from liquid diisocyanates and liquid polyether or polyester diols affords a variable motif when compared to other popular polymer systems. The step-by-step growth and synthesis afforded by polyurethanes provided a significant opportunity to build polymers with varied structures and properties. In 1952, polyisocyanates became commercially available, and commercial production of flexible PU foams began thereafter. Building on this technology, spray coating, reaction-in-molding, powder coating, and other techniques that use polyurethane polymers have greatly expanded over the past 60 years. Polyurethane polymers have shown their suitability for large surface area coatings and tank liners, and have demonstrated adhesion to concrete and steel, especially when coupled with a primer. Polyurethane polymers provide coatings that are durable, abrasion resistant, and corrosion resistant.

A polyurethane dispersion (PUD) is a free-flowing polyphasic system consisting of layers of water and polymer (e.g., a dispersed plastic). PUDs are often white translucent-to-opaque in appearance and are useful as coatings, film forming resins, and/or binders/adhesives, for example. The inherent lack of solvents in PUDs, coupled with ever increasing environmental demands, has aided their increased use and application, as well as their reputation as eco-friendly alternatives to more traditional organic solvent-based systems. The general advantages of PUDs are flexible at low temperatures, toughness, customizable mechanical properties, chemical resistance, and ability to be made hydrolytically stable. In order to impart many of these properties, it is necessary to create PUDs containing high molecular weight polymers. When the PUDs are dispersed, even those containing very high molecular weight polymers, their viscosities are determined only by the particle size (i.e., the volume fraction) in the dispersion.

Emulsions are often confused with PUDs, but emulsions result from a uniform particle size of a liquid media suspended within another immiscible liquid. In contrast, PUDs generally have a fairly broad distribution of different suspended particle sizes. Stable PUDs consist of spherical particles having a size in the range of from 30 nm to about 1,000 nm. Particles below 50 nm create a more transparent PUD, while PUDs containing particles above 1,000 nm produce a settleable solid fraction and a PUD having a very short shelf life. The contribution of the polymer solids to the total mass of the PUD is typically about 30-60%. Dispersions with high solid content have advantages in terms of transport and storage, ease of application, drying and cure times, all of which lead to a decrease of processing energy consumption. Furthermore, high solid content PUDs accentuate their environmental benefits and are becoming increasingly important.

Polyurethane densities are generally heavier than water thereby creating a tendency for the polymer to try to settle and coagulate. Coalescing forces are resisted by repulsion of the charged solubilizing groups on the particles and the attractive force that creates the systemic viscosity. In order to further combat such coagulation, PUDs may contain thickening agents and emulsifiers, which slow down the settling of the particles thereby improving shelf life. Moieties with non-ionic, cationic, and anionic hydrophilic groups can be incorporated into the polyurethane backbone or added as terminal groups in order to provide stabilization.

In addition to water, PUDs may contain hydrophilic organic solvents (e.g., N-methylpyrrolidone (NMP), glycol ethers, etc.). The addition of such a "co-solvent" enables the formation of hard polyurethane coatings by dissolving and softening the surface of the dispersed particles. After the water in the PUD is evaporated, a subsequently fused film is made (i.e., coalescence occurs). As a low vapor pressure solvent, the co-solvent evaporates gradually, allowing the film to become harder.

In order to ease the production of high molecular weight polyurethanes while preventing gelling, it is necessary to prepare these molecules maximally linear with a minimum of branching. With the materials of construction being simple bifunctional subunits, the shape, structure, and function of polyurethanes closely mirror the subunits from which the polyurethane is constructed. This creates an opportunity for the isocyanate to distinguish between aliphatic and aromatic polyurethane dispersions. Where aromatics are less expensive, they are known to yellow when exposed to light. Polyols often compose the largest mass fraction of PUDs and are generally seen as soft segments. Correspondingly, the glass transition temperature of the polyol is heavily influenced by the temperature flexibility profile.

Although PUDs generally contain the same components, the specific structures of each PUD may vary from product to product depending upon its specific structural components. As the chains are assembled, excess diisocyanate may be added, for example but without limitation, in order to provide terminal isocyanates that are further functionalized with difunctional molecules to interconnect the long-chain assemblies. The primary component of these chain assemblies is the ionic groups incorporated into the polymer to stabilize its water-dispersed particles. Dimethylol propioic acid (DMPA) results in, for example but without limitation, a polymer that is permanently hydrophilic and can be readily dispersed in an appropriate solvent system due to DMPA having carboxy and dihydroxy functionality allowing for its efficient incorporation into the backbone of the polymer while remaining functional as an ionic species. Similarly, cationic functionality can be added by combining quaternary amines such as N-methyl diethanolamine (NMDEA). Once the ionic groups (i.e., the cationic or anionic) are chosen, the particle size of the PUD can be controlled by the number of hydrophilic groups per given chain.

Typically, the preparation of a PUD in water requires a high shear force to obtain a correspondingly fine dispersion, as defined above. A common problem is the high viscosity of the undispersed isocyanate prepolymer. After chain extension, polyurethanes are practically not dispersible in water. In order to address such shortcomings, the prepolymer may be directly dispersed in water with high shear forces in the presence of the aqueous phase while heating in the presence of co-solvents. The heat may be applied to encourage dissolution or may be hot enough to melt the polyurethane into a liquid phase for dispersion. Alternatively, the co-solvent may be added directly to the solution, dispersed with water, and thereafter removed by distillation.

As previously stated, the use of PUDs are extensive. The resulting film can be dried at room temperature, or at elevated temperatures if required. After the water is evaporated, the gaps between each particle create high capillary forces that drive the particles to merge (i.e., coalescence) to form a homogeneous film. Co-solvents used to support the coalescence may remain for some time in the film after the water has evaporated. The co-solvent may also temporarily plasticize the coating and the resulting film may take some time to reach its final hardness.

Federal, state, and local regulations on the emissions of volatile organic compounds (VOCs) have pushed the use of PUDs into various industrial coatings markets including plastic, textile, leather, paper, and medical related products. These regulations have also catalyzed the expansion of PUDs into adhesives in, for example but without limitation, the shoe, automotive, and furniture industries. In many cases, these regulations have created an environment where PUDs are the preferred material because of their inherently low VOC content. Waterborne PUDs are, however, at a disadvantage as compared to solvent-based polyurethane solutions. It takes more time and/or energy to evaporate the water as compared to the VOCs used in solvent based polyurethane solutions. If one were just comparing the drying process alone, PUDs are disadvantaged when compared to solvent based polyurethane solutions. However, considering that greenhouse gases are emitted when organic solvents are used and the carbon footprint of solvent system is larger, i.e., many convert to carbon dioxide upon evaporation, the use of PUDs is becoming more routine.

As mentioned above, the growing concern about the hazardous and ecological impacts caused by the use of solvents, crosslinkers, and coalescing agents has led to the development of waterborne UV-curable polyurethane dispersions (UV-PUDs) and coatings. Ionic, isocyanate-terminated polyurethane prepolymers can be reacted with hydroxy-functional acrylates prior to dispersion into water in the presence of a neutralizing agent. Thereafter, the composition and size of the polymer chain is controlled to create the desired cross-linked content. As such, UV-PUDs are among the fastest growing coating type for wood products, for example.

Features of UV-PUDs, when compared with water/solvent free systems, retains the utility of both systems while not grossly suffering from the disadvantages of either. The UV-PUDs exhibit a delicate balance of both a strong chemical resistance (due to the UV-crosslinking) and enhanced toughness (due to the polyurethane character). The balance is struck from reduced cross-link density and thereby results in a feature set that very few coatings are able to offer: allowing for the UV-PUD to coalesce on a substrate and dry (through the loss of water) while also allowing the coating to be tack-free before curing. In this manner, such a coating affords the user the opportunity to further process the coated substrate (e.g., cutting, texturing, stamping, retreating, repairing, etc.) or even stack or roll the coated substrates for storage or shipment until subsequent UV treatment. Furthermore, balancing the crosslinking content to obtain good chemical resistance can be tipped to lower densities as polyurethane hard domains will provide additional chemical resistance. Componentry, such as mixed isocyanates and chain extenders, can also be added to the UV-PUDs in order to increase or change functionality of the UV-PUDs.

The presently disclosed and/or claimed inventive concept(s) relates to a sustainable PUD that incorporates a unique and novel blend or mixture of differing oligomeric polyols (i.e., dPET) obtained from polyethylene terephthalate that directly affects the performance characteristics of a resulting polyurethane film, adhesive, coating, and/or elastomeric material, and methods of producing the same. The presently disclosed and/or claimed inventive concept(s) also relates to the novel blend or mixture of differing oligomeric polyols and the methods of producing such.

SUMMARY OF THE INVENTIVE CONCEPT(S)

The presently disclosed and/or claimed inventive concept(s) is directed to a blend or mixture of functionalized oligomeric forms of polyethylene terephthalate (dPET) and methods of producing the same. The composition of the dPET provides a building block for polyurethanes, for example but not by way of limitation, that allows for the customization and targeting of the hard and soft regions of the resulting polymer chains. The dPET can be made from an efficient process for recovering oligomeric raw materials from waste products in economical yields. The dPET is soluble in various aqueous and organic solvents and can serve, therefore, as a specialized functional backbone for the production of polyurethanes, for example but not by way of limitation, when combined with specific ionic surfactants, non-ionic surfactants, solubilizing groups, dispersing agents, and other moieties to aid in the generation of coatings, sealants, adhesives, and elastomers. The presently disclosed and/or claimed inventive concept(s) is also directed to a sustainable PUD that incorporates the blend or mixture of differing oligomeric polyols (i.e., dPET) obtained from polyethylene terephthalate which directly affects the performance characteristics of a resulting polyurethane film, adhesive, coating, and/or elastomeric material.

BRIEF DESCRIPTION OF THE DRAWINGS

FIG. 5 shows a mixture of sterically favored and unfavored products that result in the formation of the constitutional isomers for the mono- and di-substituted terephthalate groups.

DETAILED DESCRIPTION OF THE INVENTIVE CONCEPT(S)

Figure 1:
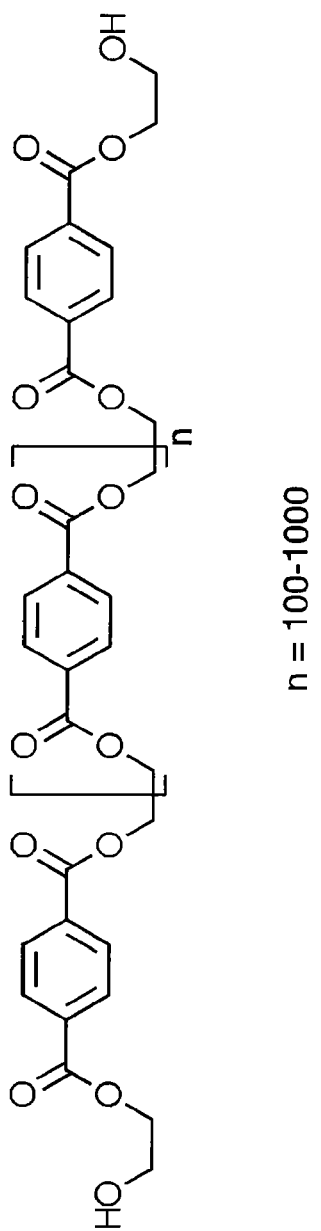
FIG. 1 is a graphical representation of the structure of polyethylene terephthalate. The structure is not dependent on the source of the polyethylene terephthalate or on whether the polyethylene terephthalate is obtained as a virgin or recycled material.

Before explaining at least one embodiment of the presently disclosed and/or claimed inventive concept(s) herein in detail, it is to be understood that the presently disclosed and/or claimed inventive concept(s) is not limited in its application to the details of construction, experiments, exemplary data, and/or the arrangement of the components set forth in the following description, or illustrated in the drawings. The presently disclosed and/or claimed inventive concept(s) is capable of other embodiments or of being practiced or carried out in various ways. Also, it is to be understood that the phraseology and terminology employed herein is for purpose of description only and should not be regarded as limiting in any way.

In the following detailed description of embodiments of the presently disclosed and/or claimed inventive concept(s), numerous specific details are set forth in order to provide a more thorough understanding of the inventive concept(s). However, it will be apparent to one of ordinary skill in the art that the inventive concept(s) within the disclosure and/or appended claims may be practiced without these specific details. In other instances, well-known features have not been described in detail to avoid unnecessarily complicating the instant disclosure. Unless otherwise defined herein, technical terms used in connection with the presently disclosed and/or claimed inventive concept(s) shall have the meanings that are commonly understood by those of ordinary skill in the art. Further, unless otherwise required by context, singular terms shall include pluralities and plural terms shall include the singular.

All patents, published patent applications, and non-patent publications mentioned in the specification are indicative of the level of skill of those skilled in the art to which the presently disclosed and/or claimed inventive concept(s) pertains. All patents, published patent applications, and non-patent publications referenced in any portion of this application are herein expressly incorporated by reference in their entirety to the same extent as if each individual patent or publication was specifically and individually indicated as incorporated by reference.

All of the articles and/or methods disclosed herein can be made and executed without undue experimentation in light of the present disclosure. While the articles and methods of the presently disclosed and/or claimed inventive concept(s) have been described in terms of preferred embodiments, it will be apparent to those skilled in the art that variations may be applied to the articles and/or methods and in the steps or in the sequence of steps of the method described herein without departing from the concept, spirit, and scope of the presently disclosed and/or claimed inventive concept(s).

As utilized in accordance with the present disclosure, the following terms, unless otherwise indicated, shall be understood to have the following meanings.

The use of the word "a" or "an" when used in conjunction with the term "comprising" may mean "one", but it is also consistent with the meaning of "one or more", "at least one", and "one or more than one". The use of the term "or" is used to mean "and/or" unless explicitly indicated to refer to alternatives only if the alternatives are mutually exclusive, although the disclosure supports a definition that refers to only alternatives "and/or". Throughout this application, the term "about" is used to indicate that a value includes the inherent variation of error for the quantifying device, the method being employed to determine the value, or the variation that exists among the study subjects. For example, but not by way of limitation, when the term "about" is utilized, the designation value may vary by plus or minus twelve percent, or eleven percent, or ten percent, or nine percent, or eight percent, or seven percent, or six percent, or five percent, or four percent, or three percent, or two percent, or one percent. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as lower or higher limits may also produce satisfactory results. In addition, the use of the term "at least one of X, Y, and Z" will be understood to include X alone, Y alone, and Z alone, as well as any combination of X, Y, and Z. The use of ordinal number terminology (i.e., "first", "second", "third", "fourth", etc.) is solely for the purpose of differentiating between two or more items and is not meant to imply any sequence or order or importance to one item over another or any order of addition, for example.

As used herein, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. The term "or combinations thereof" as used herein refers to all permutations and combinations of the listed items preceding the term. For example, "A, B, C, or combinations thereof" is intended to include at least one of: A, B, C, AB, AC, BC, or ABC and, if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABC-CCC, CBBAAA, CABABB, and so forth. The skilled artisan will understand that typically there is no limit on the number of items or terms in any combination, unless otherwise apparent from the context.

Figure 4:
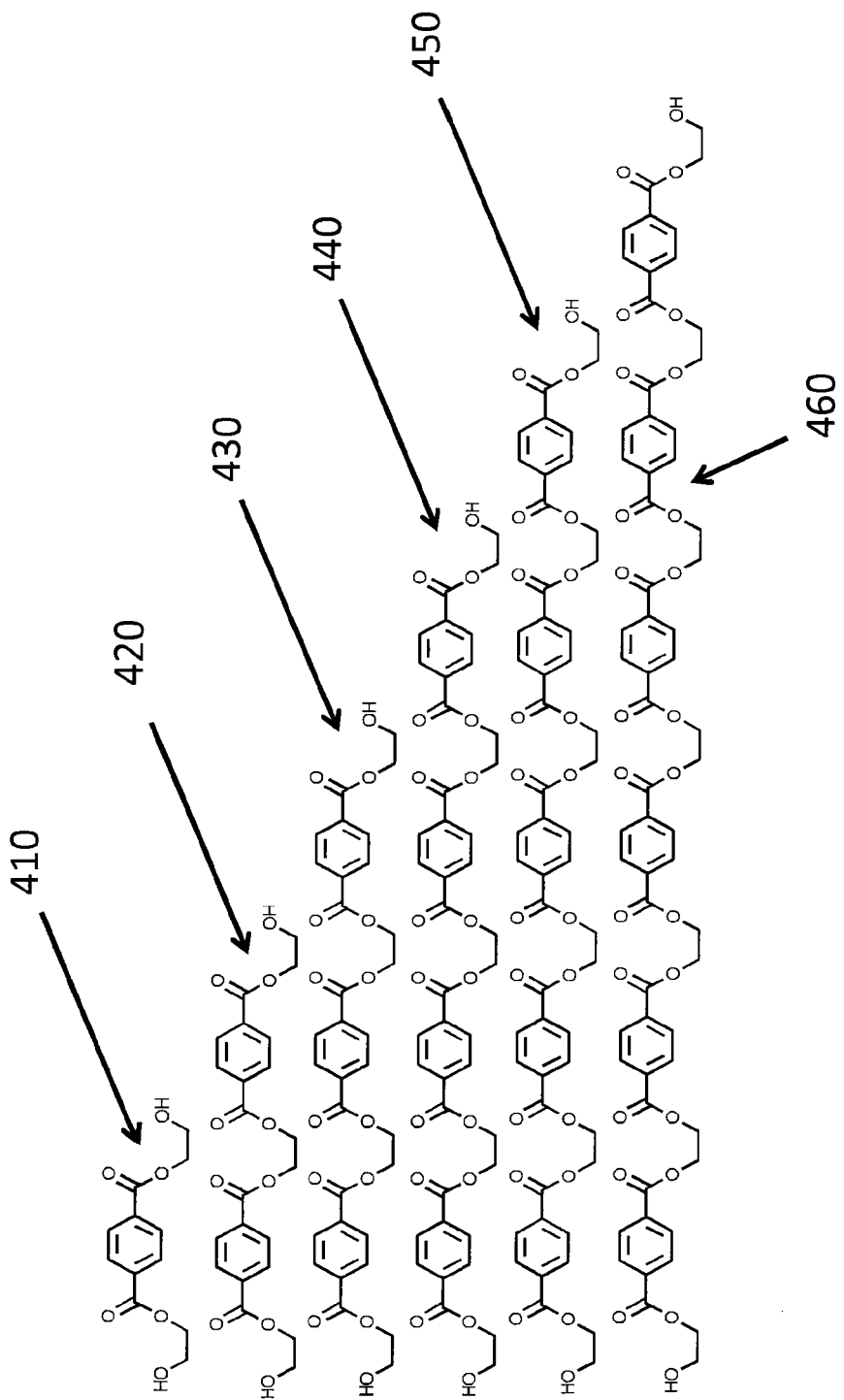
FIG. 4 is a graphical representation of structures of the resulting reaction products obtained by the glycolysis polyethylene terephthalate with ethylene glycol.
Figure 5:
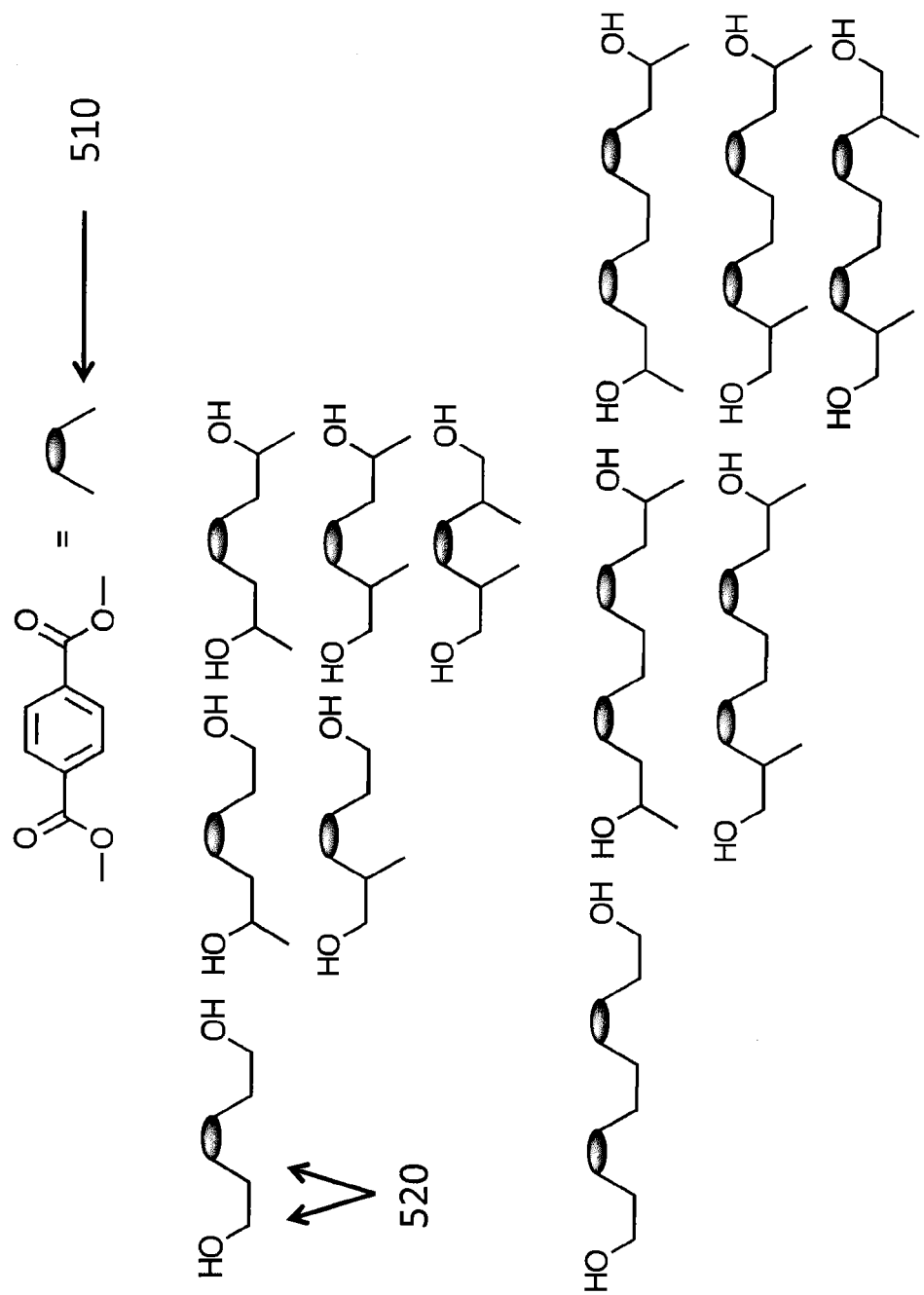
FIG. 5 is a graphical representation of the structures of the resulting reaction products of glycolysis of polyethylene terephthalate with polyethylene glycol.

In one embodiment, the presently disclosed and/or claimed inventive concept(s) encompasses a mixture or blend of oligomers that provide optimal performance for a host of polyurethane dispersions. The mixture or blend of oligomers is prepared by the reaction of polyethylene terephthalate with a glycolic molecule, i.e., a polyhydroxy functional, in the presence of a catalyst at elevated temperatures for a sufficient time to decrease the molecular weight of the polyethylene terephthalate to oligomeric species. It has been found that the reaction product of this glycolysis reaction comprises a mixture or blend of oligomers of PET (i.e., "dPET") that can be subsequently recovered individually or collectively from the reaction mixture and used to prepare, for example but without limitation, polyurethane dispersions, as illustrated by FIGS. 4 and 5. A reaction product containing a mixture or blend of differing oligomers, as described herein, is particularly well suited to coatings and adhesions made from such polyurethane dispersions.

In FIG. 4, 410 represents the structure of the fundamental piece of the polyethylene terephthalate chain to be cleaved and found in the blend or mixture of reaction products (i.e., BHET); 420 represents the structure of a species found within the blend or mixture of the reaction product having 2 TPA and 3 glycol connections making this species a "dimer"; likewise 430, 440, 450, and 460 represent trimer, tetramer, pentamer, and hexamer species, respectively. In one embodiment of the presently disclosed and/or claimed inventive concept(s), the reaction product comprises a blend or mixture of monomer, dimer, trimer, tetramer, pentamer, and hexamer polyols.

In FIG. 5, each of the represented molecules are similar in structural core but are varied on the terminal groups. For example, 510 represents the abbreviated structure of the repeated bis-functional terephthalate and 520 represents the two equivalent sites where —$CH_3$ may be present on a polyethylene glycol molecule. FIG. 5 also shows the mixture of sterically favored and unfavored products that result in the formation of the constitutional isomers for the mono- and di-substituted terephthalate groups. In an alternative embodiment, a glycol other than ethylene glycol can be used to depolymerize the polyethylene terephthalate which results in a statistical mixture of connecting and terminal glycols.

In another embodiment, such a blend or mixture of various forms of oligomeric polyols can be used to create one or more differing PUDs. Additionally, in one particular but non-limiting embodiment, the catalyst is a zinc acetate catalyst capable of increasing the rate of the depolymerization. The recovered dPET may thereafter be used as a resin component or resin extender.

The above-noted process can be used to treat a wide variety of PET polymers. For example, PET beverage containers typically cannot be reused since the elevated temperatures required for sterilization deforms the container. PET containers can, however, be ground into small pieces for use as a filler material or remelted for formation of different articles. Such recycled material may be referred to interchangeably herein as "recycled PET", "scrap PET", "waste PET", and/or "rPET". The polyethylene terephthalate recovered by such processes contains impurities, such as pigment(s), paper, metal from caps, as well as other undesirable polymers. Consequently, applications for polyethylene terephthalate reclamation by mechanical means are limited to non-food uses and low purity molded products. Though rPET is not limited to and may include whole products made of PET or further processed products made of PET, the form of the rPET when exposed to the depolymerizing conditions is often chipped or shredded to afford the desired products in a reasonable time frame. Further processing may include exotic milling or grinding of some type to the PET products in order to produce rPET material having a sufficient particle size as to aid the dissolution needed to bring the reagents together for the reactions. One of ordinary skill in the art would appreciate that the further processing step may include a multitude of processing steps, all of which would be understood to fall within the broad disclosure presented herein.

As suggested above, chemical recycling of a plastic alters the recycled material's molecular structure by chemical reaction. In one embodiment, the depolymerization of rPET into a reactive, lower melting material produces a targeted and novel mixture or blend of oligomers (dPET). When the dPET is recovered and used to form subsequent polymers (for example, but not by way of limitation, polyurethanes), the subsequent polymers have a toughness, adhesion, chemical resistance, and water stability that is improved with respect to other commercially available polymers.

The reaction scheme for depolymerization of the rPET into a reactive lower melting point material can be generally described as being influenced by the following components and procedural steps: (1) the amount and type of glycol used will heavily influence the content of the glycol products, and (2) the oligomers are generated by a recombination of the monomeric BHET into higher molecular weight structures. The presently disclosed and/or claimed inventive concept(s) differentiates itself from the prior art which teaches the use of singular or stratified oligomeric species as starting materials. Additionally, the presently disclosed and/or claimed inventive concept(s) can produce oligomers from ethylene oxide or epichlorohydrin and terephthalic acid, unlike previous processes as disclosed in U.S. Pat. Nos. 1,883,182 and 2,335,813. Furthermore, it has been determined by the presently disclosed and/or claimed inventive concept(s) that the presently disclosed and/or claimed inventive concept(s) is directed to a process capable of controlling the removal of byproducts and other impurities formed during the depolymerization of PET, which shortens the reaction time for depolymerization, ensures reaction completion, and ensures that the blend of oligomers produced are of a suitable product quality.

Non-limiting examples of the depolymerization of rPET into a reactive lower melting point mixture or blend of oligomers (i.e., dPET) that provides optimal performance for a host of polyurethane dispersions, as described above, is exemplified by the following procedures for digesting both virgin and recycled PET with propylene glycol using methods that both require and do not require the removal of byproducts during the reaction.

Process of Digesting rPET without Removing Byproducts During the Reaction

A 2 L, 4-neck flask was equipped with a mechanical stirrer, thermocouple, condenser and stopper. Propylene glycol (267.6 g, Dow lot#1D0301N6DA) was added to the flask. Zinc acetate dihydrate (14.12 g, Sigma Aldrich) was added in one portion. rPET flakes (750.26 g, Evergreen Plastics lot #43004930) were added in portions over a 15 min. period such that the glycol to PET ratio was at approximately 0.9 molar equivalents. The temperature was raised to >190° C. and held for 4.0 h. The reaction was deemed complete when a dark translucent fluid, with few pieces of undigested particulate matter, predominantly filled the reactor. The flakes dissolved to give a slightly hazy solution. The reactor contents were allowed to cool to 120° C. The dPET was then filtered to remove undigested PET and contaminants, then stored in a tightly sealed container. The resulting dPET was observed to have a hydroxyl number of 357 (over an average of three determinations), while the viscosity was measured to be <13,000 centipoise (cP) at 80° C. The GPC data indicated that the resulting dPET produced the characteristic distribution of peaks (See FIG. 6).

The dPET reaction product was characterized by differential scanning calorimetry (DSC), gas chromatography with mass spectroscopy (GC-MS), fourier transform infrared spectroscopy (FTIR), viscosity, hydroxyl end-group titration (OH number) and gel permeation chromatography (GPC) to reveal that the resultant was composed of a variety of PET-related oligomers. Modulated DSC (mDSC) was used to determine the material's melting point. A melt occurring at 109° C. indicated, moreover, that a minor amount of BHET (FIG. 8, mDSC heat flow) was also present in the dPET. This melting point is consistent with commercially available BHET material supplied by Sigma Aldrich Co. (CAS#959-26-2). The data demonstrates that an atmospheric pressure based system can be used to depolymerize rPET into dPET. The data shows that the reaction product (i.e., dPET) is non-uniform in molecular weight and composition, and comprises a mixture or blend of differing oligomers. The analysis indicated that if the reaction conditions are modified, the dPET will have differing distributions of oligomers.

Figure 2:
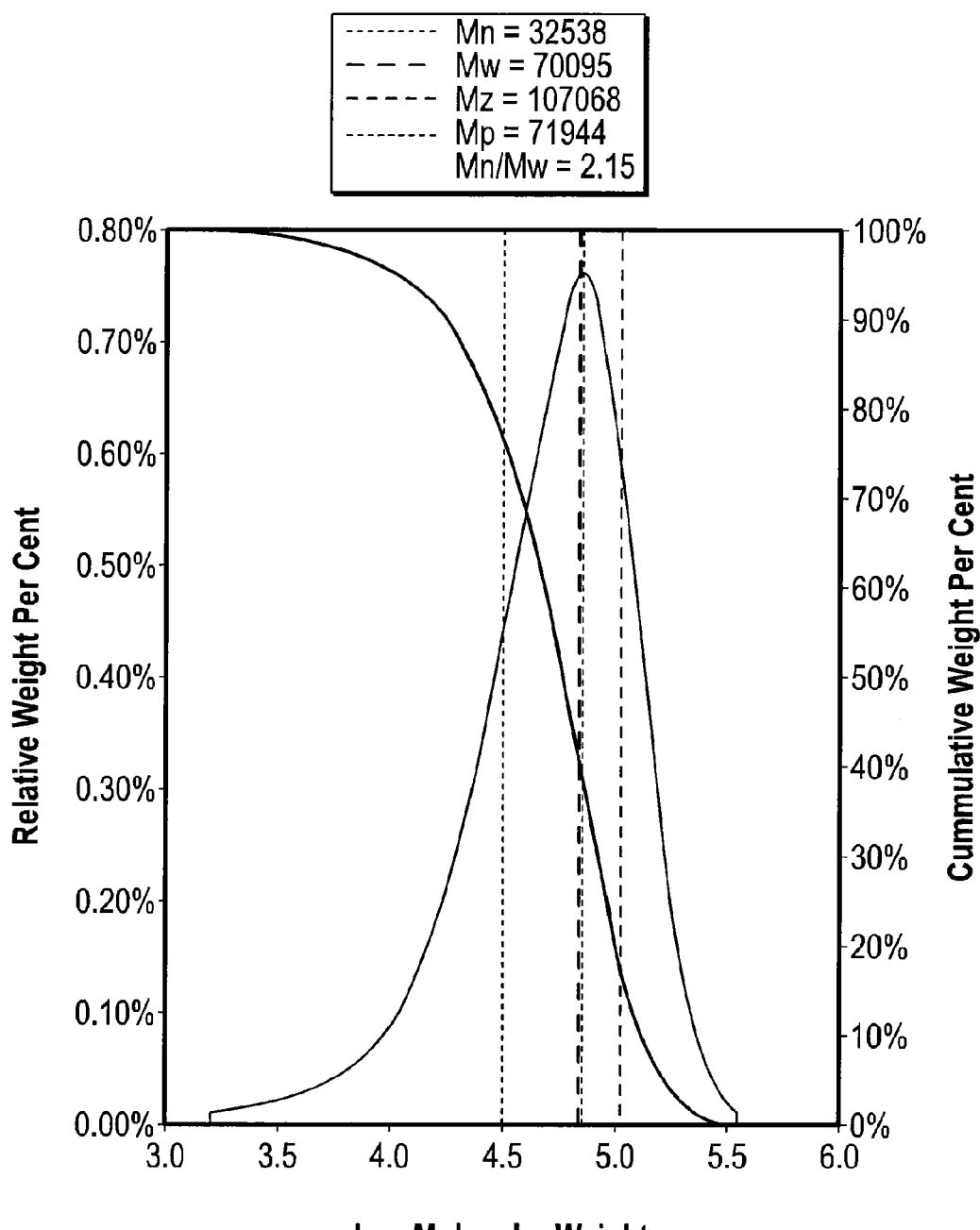
FIG. 2 is a graphical representation of the GPC of recycled polyethylene terephthalate prior to depolymerization, indicating that the MW, Mn, and Mp of the recycled polyethylene terephthalate are all above 20,000 Daltons.
Figure 3:
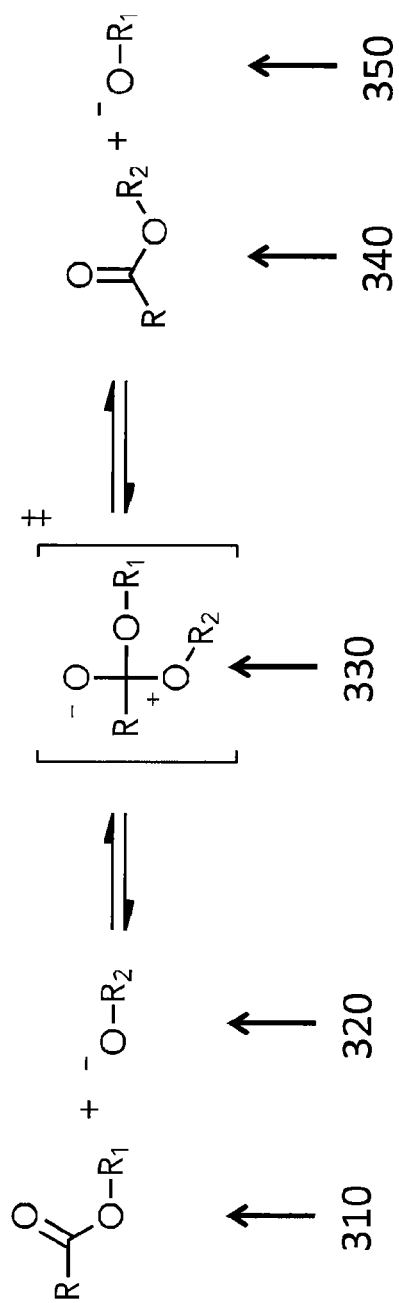
FIG. 3 is a graphical representation of the reaction chemistry demonstrating a generic model of hydrolysis, methanolysis, and glycolysis of polyethylene terephthalate indicating their similarity.

The manipulation of the reagents has shown that changing the ratio of terephthalic acid to transesterification glycol creates a final product with an equivalently varied average molecular weight (MW). In order to obtain a lower molecular weight rPET species, the reactions were designed such that every additional mole of glycol added would be capable of reducing the molecular weight of the polymer through transesterification. Although the starting MW of PET is approximately 20,000-100,000 Daltons (FIG. 2), the MW of the individual oligomers comprising the dPET is in a range of from about 200 to about 2,000 Daltons.

Figure 6:
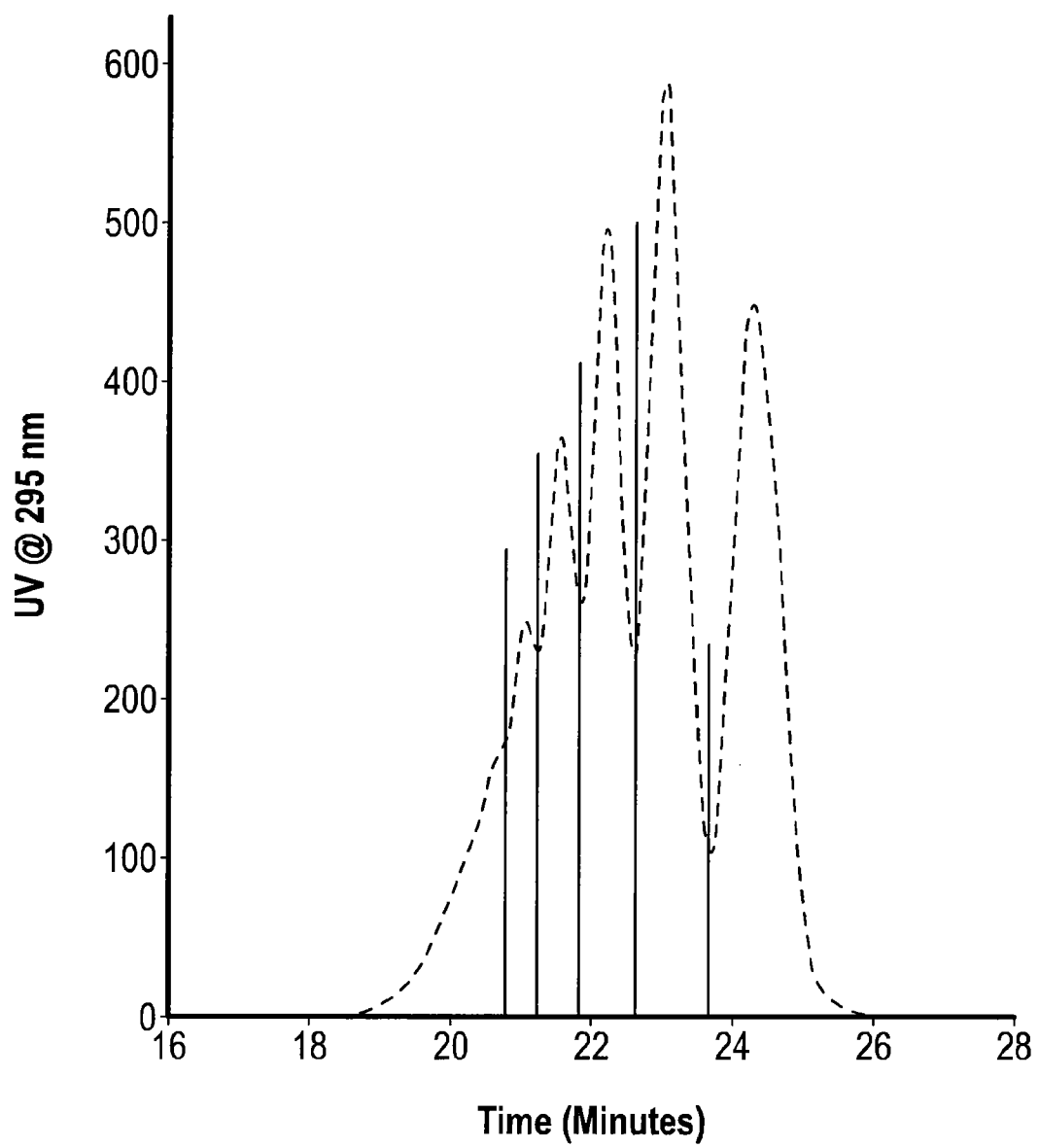
FIG. 6 is a graphical representation of a GPC of a digestion of polyethylene terephthalate demonstrating propylene glycol, reacted at 0.8 molar equivalents relative to the terephthalate repeat unit in the polymer, yields a mixture of monomers, dimers, trimers, tetramers, pentamers, and hexamers found in the reaction product.

The exemplary reactions given above were considered to be complete once the pellets of rPET were completely dissolved and the reaction reached a homogeneous, liquid phase. In each case, this required >2 hours of reaction time. Upon termination of the reactions, the mixture or blend of recovered oligomeric units of rPET (i.e., the dPET) primarily comprised incompletely digested oligomers of rPET. Chromatography elucidated the molecular weight and distribution of the oligomers of rPET found in the dPET. As is common for GPC analysis of PET, the samples were analyzed in comparison to polystyrene MW calibration standards. Replicate preparations of the dPET were analyzed. The results showed that the molecular weight of the rPET had been reduced from approximately 70,000 ($M_p$) (FIG. 2) to a mixture or blend of oligomers (i.e., the dPET) ranging from about 200 to about 2,000 Daltons and being discrete molecular species (FIG. 6). Though the composition of these specific molecular structures vary by the connectivity and symmetry of the glycol used for the digestion (FIG. 5), the products are discrete molecular entities, and show very low polydispersities.

Figure 7:
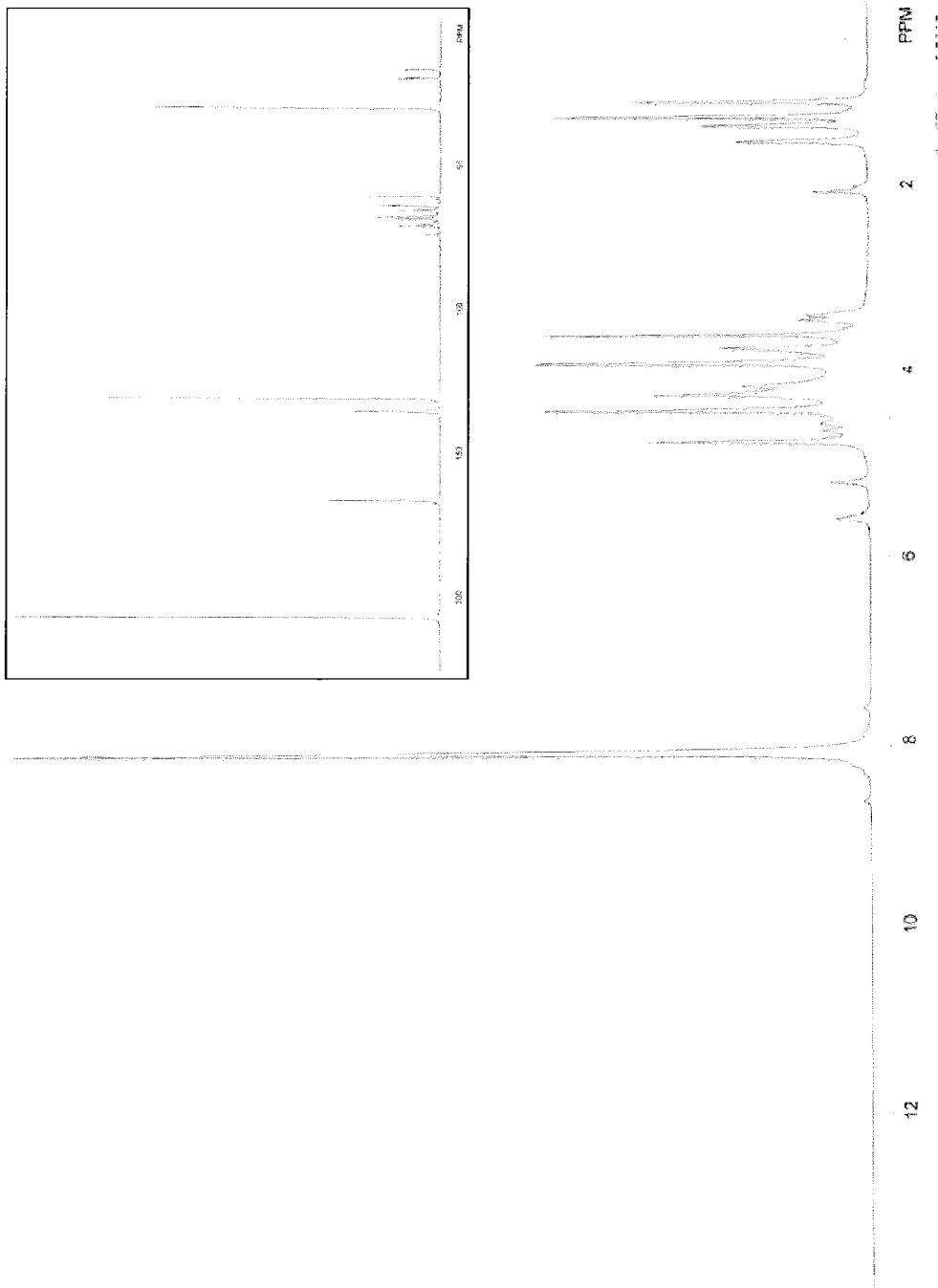
FIG. 7 is a graphical representation of the NMR of the reaction products of a digestion of polyethylene terephthalate with propylene glycol, reacted at 1.0 molar equivalents relative to the terephthalate repeat unit in the polymer, yields the proton and carbon-13 spectra thereof.
Figure 8:
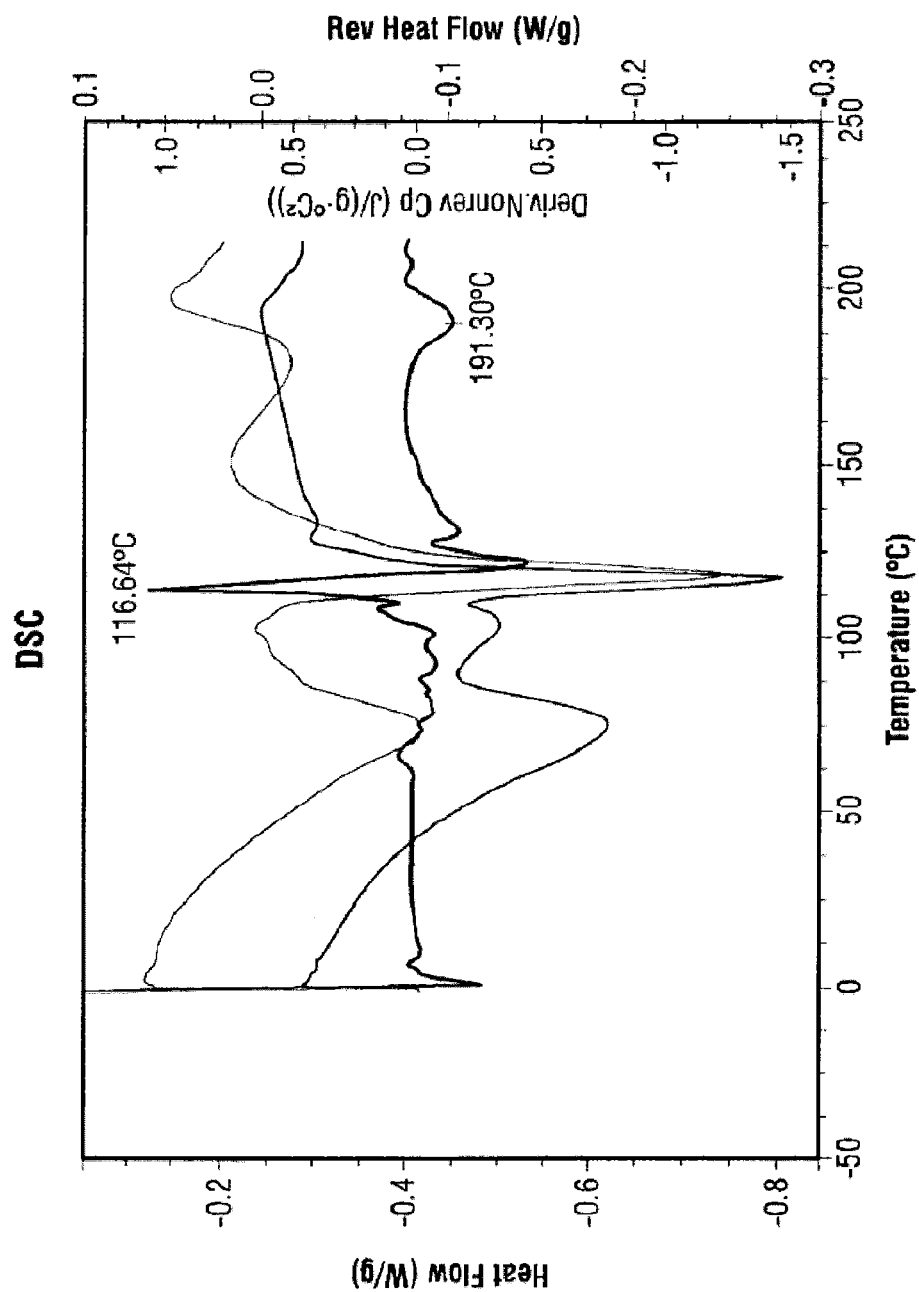
FIG. 8 is a graphical representation of the DSC of the reaction products of a digestion of polyethylene terephthalate with neopentyl glycol, reacted at 1.0 molar equivalents relative to the terephthalate repeat unit in the polymer, yields associated endo- and exo-therms of the components.
Figure 9:
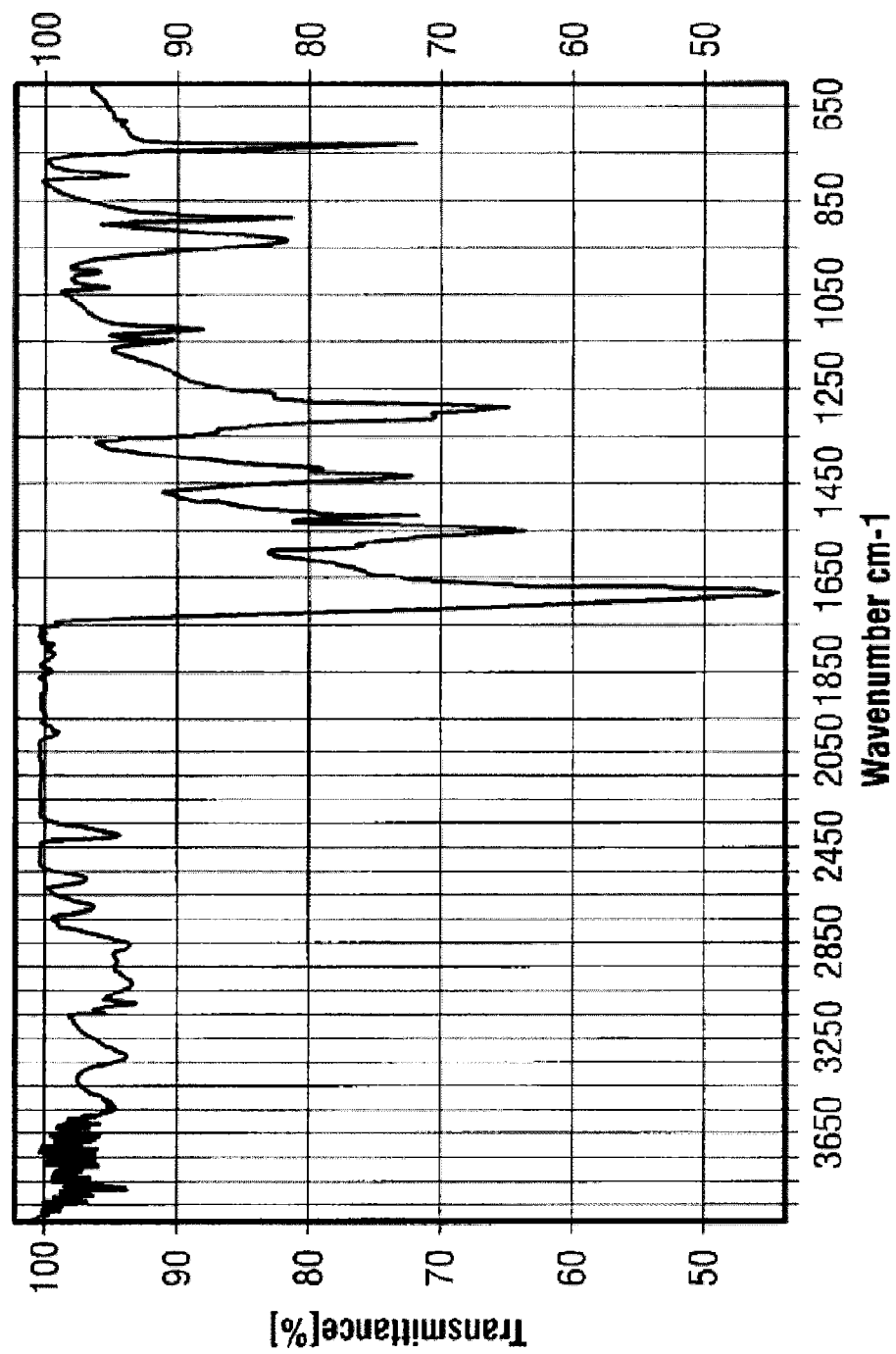
FIG. 9 is a graphical representation of the FTIR of the reaction products of a digestion of polyethylene terephthalate with propylene glycol, reacted at 0.9 molar equivalents relative to the terephthalate repeat unit in the polymer, which yields the characteristic absorption stretches of the components.

Although not wishing to be bound by a particular theory, it is believed that the mixture or blend of oligomers found in the dPET is due to the glycol being used for digestion being different from the evolved glycol found in the rPET chain. As such, there is an opportunity for an oligomer produced according to the reaction processes described above to possess two different glycolic groups. As such, the slight variations in polydispersity can be explained. The DSC, $^1$H and $^{13}$C-NMR, and FTIR analysis of the resulting dPET showed that the rPET reacted completely (FIGS. 7, 8, and 9, respectively). The observation that the dPET contains oligomers of differing size and structure is also confirmed by end group hydroxide titration quantitation of the reaction products (i.e., the dPET) which, when tested, correlates with the GPC data.

To understand the chemistry of the mixture or blend of oligomers found in the dPET, it was necessary to perform gel permeation/size exclusion chromatography (GPC) on the above-described dPET. GPC analysis was performed by dissolving aliquots of the dPET in tetrahydrofuran (THF) with shaken agitation until the mixture appeared to be evenly dispersed with no large pieces or agglomerations. This mixture was then able to be injected and analyzed via GPC using Waters 500 Å, Waters 1,000 Å, and Waters 10,000 Å (or the equivalent) with a THF mobile phase. The resulting eluent was selectively detected using UV light between about 250-300 nm, which was capable of detecting the aromatic groups in the reaction products. Then, by correlating time to molecular weight and using polystyrene standards for calibration purposes, the shape of each peak on the given column set(s) was used to determine the weighted average and number average molecular weights of the reaction products in the eluent.

The above-described GPC analysis was also carried out on several additional dPETs produced by the procedure set out above, varying the molar ratio of propylene glycol to rPET from 0.45 to 2.5. The chromatographic profile for the dPET products is presented in FIG. 10 which plots the percent relative peak area versus the molar equivalence of glycol added to the reaction. The intensity of the peaks, i.e., the peak area on the x-axis, is indicative of the molecular weights of the components in the reaction product making it possible to determine the terephthalate repeat units of the components in the dPET.

Figure 10:
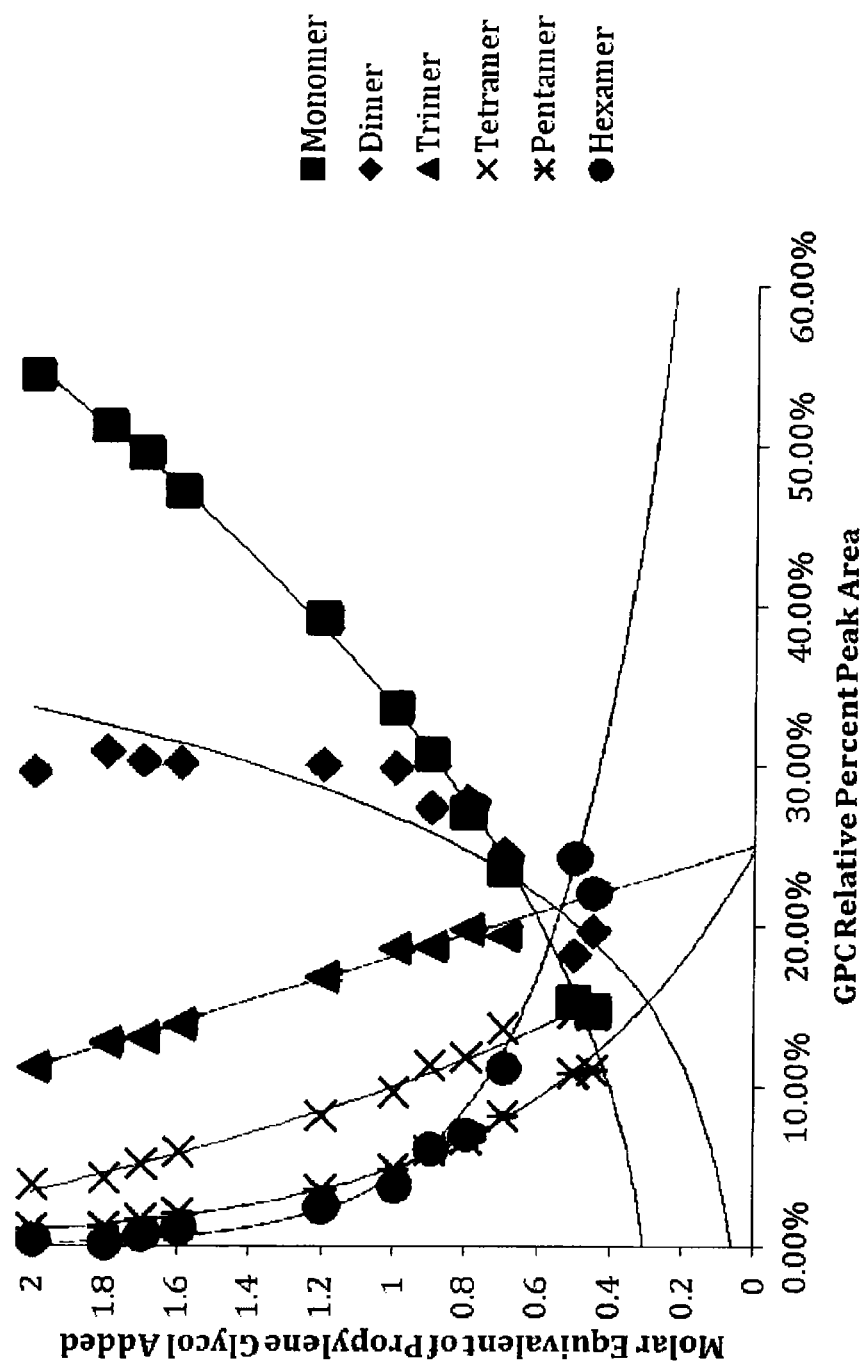
FIG. 10 is a graphical representation of the molar equivalence of propylene glycol to PET versus the relative percent areas of specific oligomer materials identified by GPC analysis.

From FIG. 10, it can be seen that as the amount of glycol is varied, trend lines can be materialized from the plot. These trend lines can be tracked for all of the measured oligomers (i.e., monomers, dimers, trimers, etc.) and, thereby, provide a means for accurately assessing the composition and quality of the resulting product. Additionally, FIG. 10 illustrates the above-mentioned feature that the molar ratio of glycol to PET heavily impacts the quality of the resultant mixture or blend of oligomers in the dPET. As the parent PET is cut by the hydroxyl-containing molecules with the aid of the catalyst, the symmetry of the hydroxyl molecule becomes relevant in accounting for the makeup of the products.

Thus, a molecule like ethylene glycol will result in equivalent molecules of monomers, dimers, trimers, etc., regardless of the hydroxyl that reacts. However, a molecule like propylene glycol will have a preference to react at the less hindered side in approximately a 2 to 1 excess, which creates a statistical mix of favored and unfavored products for the monomer, dimer, and all the other oligomers produced. Additionally, when the rPET is glycolized by a glycol other than ethylene glycol, only one of the two resulting oligomers will possess the new glycol and the other will be an ethylene glycol terminal from the native PET. When using propylene glycol, the result is a collection of molecules that range in mass from 254 to 282 g/mol having di-favored substitution, mono-favored substitution, and di-unfavored substitution present. For monomers, these effects can be seen in a pronounced way. For example, a >10% increase in mass can be measured when using propylene glycol for glycolysis due to glycol insertion and changes of the dipole from the favored and unfavored reaction products, despite the GPC showing only a single peak with very little signs of various species co-eluting in the monomer and no signs of such in the other observed peaks.

As such, the composition of the profile presented in FIG. 10 is heavily influenced by the reaction conditions including time, catalyst load, and temperature as well as other factors that may impact the kinetics of the depolymerization. In one non-limiting example, it was observed that in order to initiate the depolymerization reaction of rPET with propylene glycol in a 0.9:1 ratio, the temperature needed to be high enough to homogenize the PET media irrespective of the amount of catalyst present. However, as the temperature was raised to a sufficient level to initiate the reaction, the sustained heating of the reaction mixture encouraged the formation of glycol side reaction products that consumed the glycol and degraded the quality of the product. These side reaction products, i.e., byproducts, were removed in a waste stream, analyzed, and identified using GPC and are presented in Table 1.

TABLE 1

GC-MS Identified Components of Byproducts

| Byproduct | Relative % in Waste Stream |
| --- | --- |
| 1,4-dioxane | <5 |
| 2-methyl-1,4-dioxane | >10 |
| 2,6-dimethyl-1,4-dioxane | >10 |
| 2,5-dimehtyl-1,4-dioxane | >10 |
| Propylene Glycol | <10 |
| Ethylene Glycol | <10 |
| Acetone | <5 |
| Products of acetate and glycol | <5 |

The formation of these byproducts was determined to be unavoidable and as the reaction ran at higher temperatures, the formation of the byproducts became more prevalent. It was determined that these byproducts were caused by reactions of glycols to form cyclic dimers and dimer related isomers, and also by a trace amount of side reactions with the catalyst. It was also determined that the byproducts and other impurities formed during the depolymerization of rPET need to be removed from larger scale reaction processes due to their low boiling points directly impacting the reaction temperature of the process. Although these byproducts are not necessarily impediments to the formation of dPETs at the laboratory scale (primarily due to the favorable ratio of headspace to volume of lab scale reactors), these byproducts can be impediments to the formation of dPETs at larger reaction scales where the ratio of headspace to reactor volume is no longer favorable.

Figure 11:
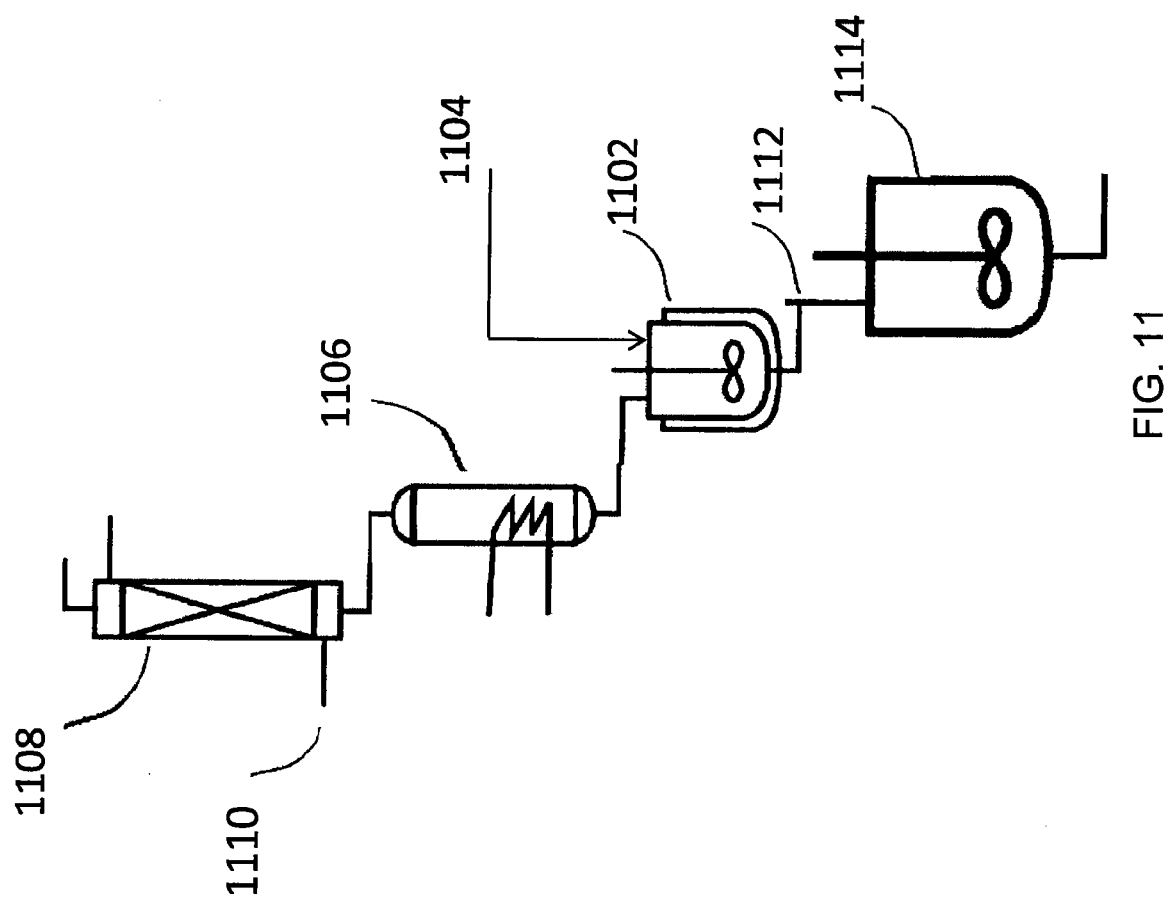
FIG. 11 is a graphical representation of a process for depolymerizing rPET into a mixture or blend of oligomers wherein the process is capable of controlling the removal of the byproducts and other impurities formed during the depolymerization reaction.

Therefore, in an alternative embodiment, the presently disclosed and/or claimed inventive concept(s) relates to a process for depolymerizing rPET into a mixture or blend of oligomers wherein the process is capable of controlling the removal of the above-described byproducts and other impurities, as exemplified by the non-limiting example presented in FIG. 11. By controlling the removal of byproducts and other impurities formed during the depolymerization of rPET, the overall reaction time for depolymerization of the rPET is shortened, while still ensuring reaction completion and that the dPET produced is of a suitable quality for further uses.

Process of Digesting rPET with the Removal of Byproducts During the Reaction

FIG. 11 represents a general process flow chart for a process of depolymerizing rPET into a mixture or blend of oligomers wherein the process is capable of simultaneously removing the byproducts and other impurities formed by the depolymerization reaction. In one embodiment, the jacketed reactor 1102 contains a glycol and a catalyst(s) and rPET is supplied to the reactor via pipe 1104. The jacketed reactor 1102 is outfitted with a heated/cooled riser pipe 1106 to create a vapor hurdle to assist in controlling the reaction temperature. The heated/cooled riser pipe 1106 allows a vapor hurdle to be created by controlling the temperature of the vapor produced by the reaction and the rate at which the vapor is removed. At the onset of the reaction, the riser pipe 1106 is used to distill any initial moisture out of the system. If the moisture is not removed from the reaction system, the moisture can accumulate in the reaction system and cause depression of the reaction temperature resulting in a longer reaction time and a degradation of the dPET produced. Once the moisture and other miscellaneous low boiling entities have been distilled off, the temperature of the riser pipe 1106 can be increased. The increase in temperature is sufficient to encourage the byproducts to emerge from the head space of the jacketed reactor 1102 and travel through the riser pipe 1106 to a condenser 1108 where the byproducts are cooled to liquid temperatures and collected in the distillate stream 1110 and removed from the system. The increase in the temperature of the riser pipe 1106 must be done with care such that it is not done too early or too late in the reaction. If the temperature of the riser pipe 1106 is increased too early, glycol is unnecessarily removed from the reactor and negatively impacts the amount of glycol available to depolymerize the rPET. If the temperature of the riser pipe 1106 is increased too late in the reaction, the dPET may be contaminated with an excessive amount of the byproducts referenced above.

Figure 12:
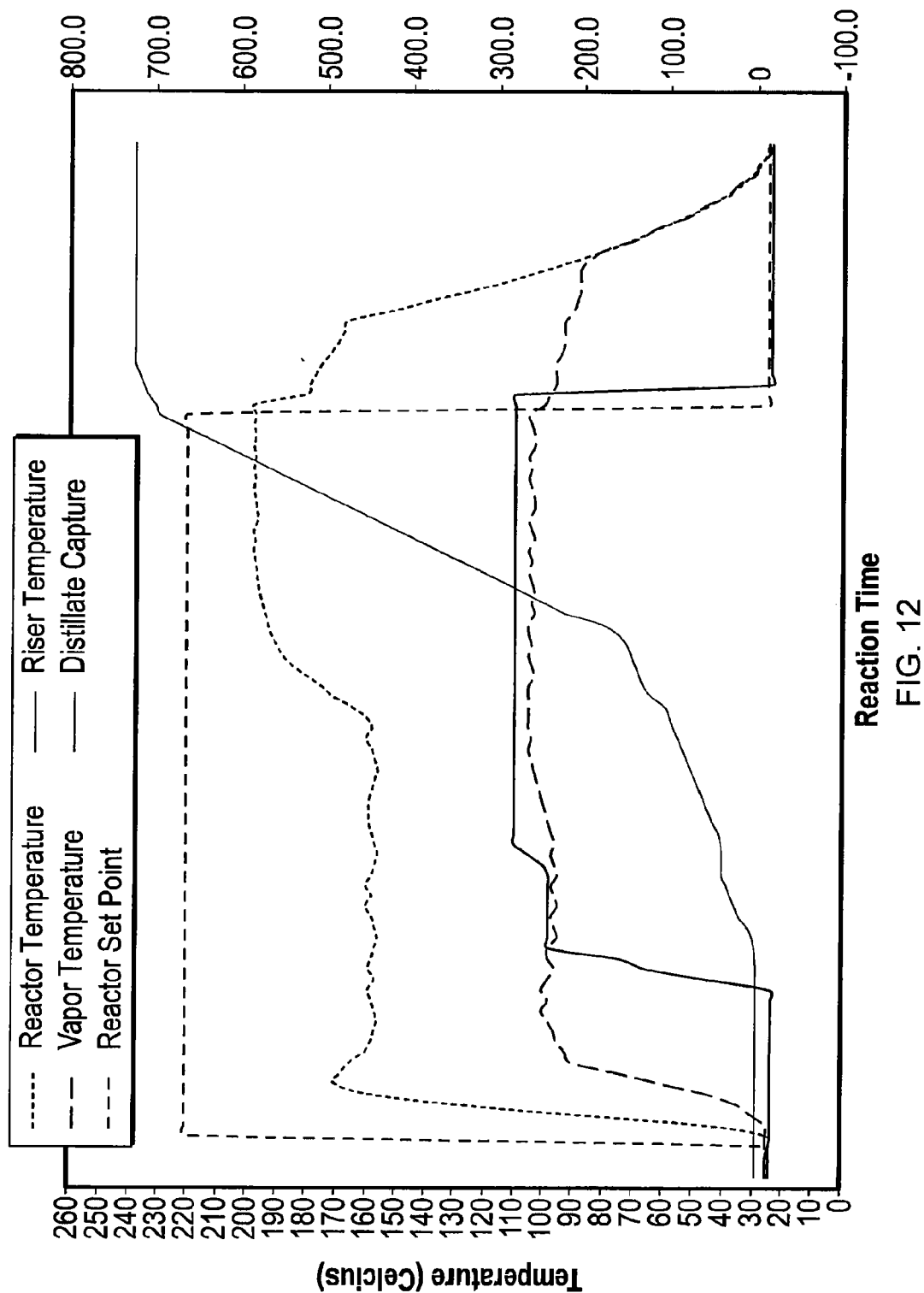
FIG. 12 is a graphical representation of the temperature trends, including the reaction stall temperature and relationship of the vapor temperature to the reaction temperature, necessary to run a process for depolymerizing rPET into a mixture or blend of oligomers wherein the process is capable of controlling the removal of the byproducts and other impurities formed during the depolymerization reaction.

FIG. 12 illustrates, in a non-limiting example, the temperature trends necessary to run the process, including the reaction stall temperature and relationship of the vapor temperature to the reaction temperature. Additionally, FIG. 12 illustrates the need to have a steady flow of distillate comprising the byproducts. Once the reaction has reached completion, the product is filtered through a coarse woven filter in pipe 1112 and transferred via pipe 1112 to another tank reactor 1114 for subsequent reactions and/or processing.

In one non-limiting example of the above-described system, glycol and rPET are supplied into the reactor 1102 in the presence of a carbonyl-coordinating catalyst to increase the rate of glycolysis. The catalyst can be, for example but without limitation, a transesterification catalyst, wherein the transesterification catalyst comprises, consists of, or consists essentially of a salt comprising, consisting of, or consisting essentially of at least one of manganese, zinc, antimony, titanium, tin, germanium, and combinations thereof. The glycol can be a hydroxy-containing organic molecule generally comprising a modified glycol having between about 2 to about 10 carbon atoms. For example, but without limitation, the glycol can be selected from the group comprising, consisting of, or consisting essentially of at least one of ethylene glycol, propylene glycol, 1,3-propanediol, 1,4-butanediol, 1,6-hexanediol, diethylene glycol, 1,4-cyclohexanediol, and 1,4-cyclohexanedimethanol, and combinations thereof. In one embodiment, the glycol can be a recycled hydroxyl-containing organic molecule generally comprising a modified glycol between about 2 to about 10 carbon atoms. For example, but without limitation, the glycol can be selected from the group comprising, consisting of, or consisting essentially of at least one of recycled ethylene glycol, recycled propylene glycol, recycled 1,3-propanediol, recycled 1,4-butanediol, recycled 1,6-hexanediol, recycled diethylene glycol, recycled 1,4-cyclohexanediol, recycled 1,4-cyclohexanedimethanol, and combinations thereof. Additionally, the form of rPET used in the process can comprise, consist of, or consist essentially of film, lump, fiber, chip, pellet, and combinations thereof. In order to obtain depolymerization products (dPET) with desired characteristics, the molar ratio of glycol to rPET added to the reactor 1102 can be in the range of from about 0.7 to about 2.0, or from about 0.8 to about 1.5, or from about 0.85 to about 1.0. If the molar ratio of glycol to rPET is less than 0.7, the dPET obtained from the depolymerization reaction can be too low in quality due to a lack of solubility and therefore is unable to be further reacted and used in various applications. If the molar ratio of glycol to rPET is greater than 2.0, the composition of the resultant mixture or blend of oligomers can be negatively affected and the desired properties caused by the variety of molecular weights are lost.

In the above-recited non-limiting example, illustrated by FIG. 11, the glycol, rPET, and carbonyl-coordinating catalyst are depolymerized under agitation in the reactor 1102 at a temperature of about 180° C. The riser 1106 and condenser 1108 are initially set at a low enough temperature to allow the reaction temperature to stall at or below 180° C. The riser 1106 temperature is then increased to and maintained at a temperature in the range of from about 95° C. to about 100° C. until the reaction temperature (i.e., the temperature of the reactor 1102) increases to a range of from about 180° C. to about 210° C., and is thereafter maintained within that range until material is captured by the condenser. Then, the riser 1106 temperature is increased to and maintained at a temperature in the range of from about 100° C. to about 110° C. in order to increase the reaction temperature to about 210° C. and thereafter collect about 5-10 g of condensed vapor for every pound of product produced, wherein the condensed vapor comprises the above-described byproducts of the depolymerization reaction. Additionally, the gauge of 5-10 g of condensed vapor (i.e., the waste stream) per pound of reaction product can be used to set temperatures, but is highly dependent on the manifold and overhead plumbing and construction which heavily influence the retention or release of headspace vapors.

The above-described process of removing unwanted byproducts during the depolymerization reaction leads to a shortened depolymerization time, alleviates the need to run the reaction in a pressurized vessel to confine the glycol, creates a unique blend of aromatic ester oligomers of dPET, and results in an economic advantage due to the controlled consumption of glycol and the production of a usable mixture or blend of oligomers of PET. FIG. 10, as described above, is also applicable for the dPET reaction products produced by the above-described process and provides a means for accurately assessing the composition and quality of the resulting product.

The byproducts in the waste distillate stream 1110 of the above-described process were analyzed using gas chromatography and mass spectrometry. Tables 2 and 3 present the byproducts that were continuously removed from the reaction during the depolymerization of rPET with propylene glycol. The waste distillate stream 1110 generally comprises two immiscible layers: a less dense clear faint yellow layer and a denser colorless clear layer. The faint yellow layer and the dense colorless clear layer were analyzed to determine their compositions; the results of which are presented in Tables 2 and 3, respectively. It was imperative to remove the byproducts at an optimal rate to encourage the reaction to proceed but not so quickly as to significantly decrease the glycol concentration such as to impact the desired oligomers in the dPET.

TABLE 2

Composition of Faint Yellow Layer

| Byproduct | Relative % in Waste Stream |
| --- | --- |
| 2,6-dimethyl-1,4-dioxane and 2,5-methyl-1,4-dioxane | >30 |
| 2-methyl-1,4-dioxane | >30 |

TABLE 2-continued

Composition of Faint Yellow Layer

| Byproduct | Relative % in Waste Stream |
| --- | --- |
| Mixture of Propylene Glycol, Ethylene Glycol, Diethylene Glycol, and Condensation Ethers thereof | >25 |
| Acetone | >5 |
| Mixture of Propylene/Ethylene/Diethylene Glycol-Esters | Trace |

TABLE 3

Colorless Clear Layer

| Byproduct | Relative % in Waste Stream |
| --- | --- |
| Water | >70 |
| Mixture of Propylene Glycol, Ethylene Glycol, Diethylene Glycol, and Condensation Ethers thereof | >10 |
| 2-methyl-1,4-dioxane | >5 |
| 2,6-dimethyl-1,4-dioxane and 2,5-methyl-1,4-dioxane | >5 |
| Mixture of Propylene/Ethylene/Diethylene Glycol-Esters | Trace |

Digestion of Virgin PET

While the aforementioned describes the impact of treatment with rPET, the reaction processes may also be performed with virgin PET ("vPET"—i.e., polyethylene terephthalate that has not previously been molded into a product, a previously molded PET product that has not been commercially used, a previously molded PET product that has been used to hold a product or act as packaging but has not been put into commercial streams of commerce, and combinations thereof). As such, the term rPET should be understood as encompassing polyethylene terephthalate material having a recycled content of from 0% to 100% and still be within the scope of the presently disclosed and/or claimed inventive concept(s).

Process of Digesting Virgin PET without the Removal of Byproducts During the Reaction A 1 L, 4-neck flask was equipped with a mechanical stirrer, thermocouple, condenser and stopper. Neopentyl glycol (129.3 g, Aldrich 538256 lot#07304DHV) was added to the flask and melted. All of the solids dissolved when the flask was at 95° C. (internal temperature). Zinc acetate dihydrate (3.85 g, Alfa Aesar 11559, lot # C11W013) was added in one portion. The temperature was increased to 135° C. and virgin PET (i.e., vPET—240 g, Poly Sciences 04301 lot #46418) was added in portions over a 15 min period. The temperature was raised to 200° C. and held for 4.5 h. The pellets dissolved to give a slightly hazy solution—i.e., dPET obtained from a reaction of vPET. The resulting dPET from vPET was observed to have a hydroxyl number of 354 (over an average of three determinations) which corresponds to 6.31 mmol/g while the viscosity was measured to be 1416 cP at 80° C. GPC data indicated that the resulting dPET from vPET had an average MW of 1237 g/mol and the resulting chromatograph was similar to dPET from a rPET source that was digested in a similar manner. Overall, the data for virgin digested material was consistent with material prepared from recycled PET using the same stoichiometry.

Process of Digesting Virgin PET with the Removal of Byproducts During the Reaction The process described above for digesting rPET while removing the byproducts in a waste stream can also be run using vPET as the starting material for depolymerization. Overall, the process is consistent with that described above and provides a dPET reaction product consistent with that produced using rPET as the starting material keeping the glycol/PET stoichiometry the same.

Figure 13:
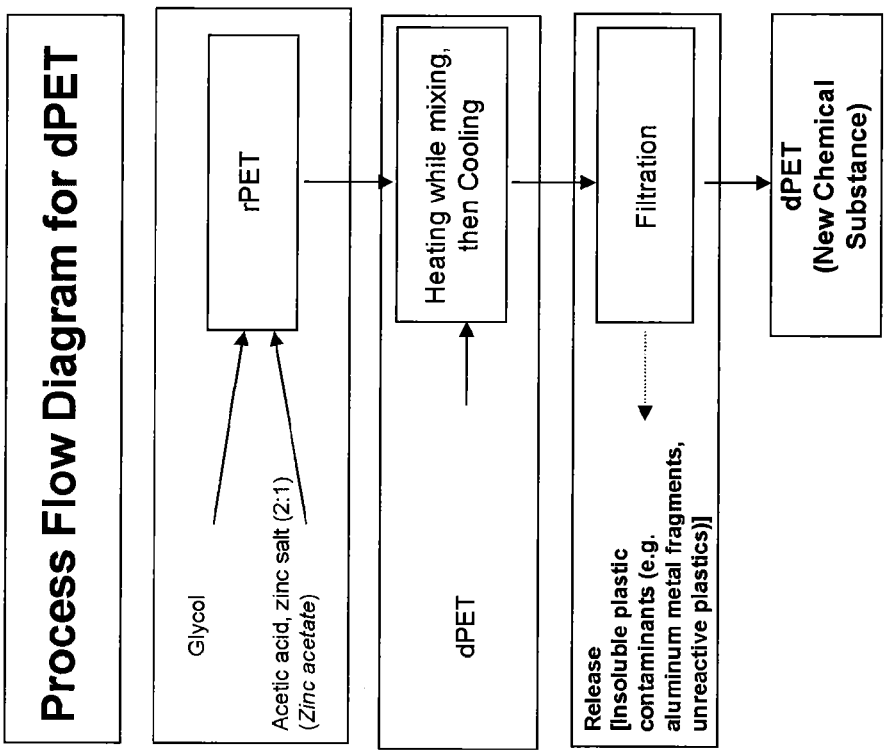
FIG. 13 is a graphical representation of an exemplary process flow diagram for the production of reaction products via the digestion of polyethylene terephthalate.

The overall process for the manufacture of dPET lends itself to scalability (FIGS. 11 and 13), and can be envisioned as a batch or continuous process to make the resulting dPET. One skilled and trained in the art might assemble a process flow chart as described in FIGS. 11 and 13, which illustrates the full production process.

Polyurethanes Comprising dPET

Physical properties of films made from polyurethanes comprising dPET indicate that dPET based polyurethanes are suitable for commercial applications. Polyurethane prepolymers used in making polyurethane dispersions require a polyisocyanate component and an isocyanate reactive component (also known as an active hydrogen containing material or polyols). Polyurethanes earned their nomenclature by being polymers that possess interconnects or terminal groups of the functional moieties of urea, polyureas, allophonate, biuret, and others.

Figure 14:
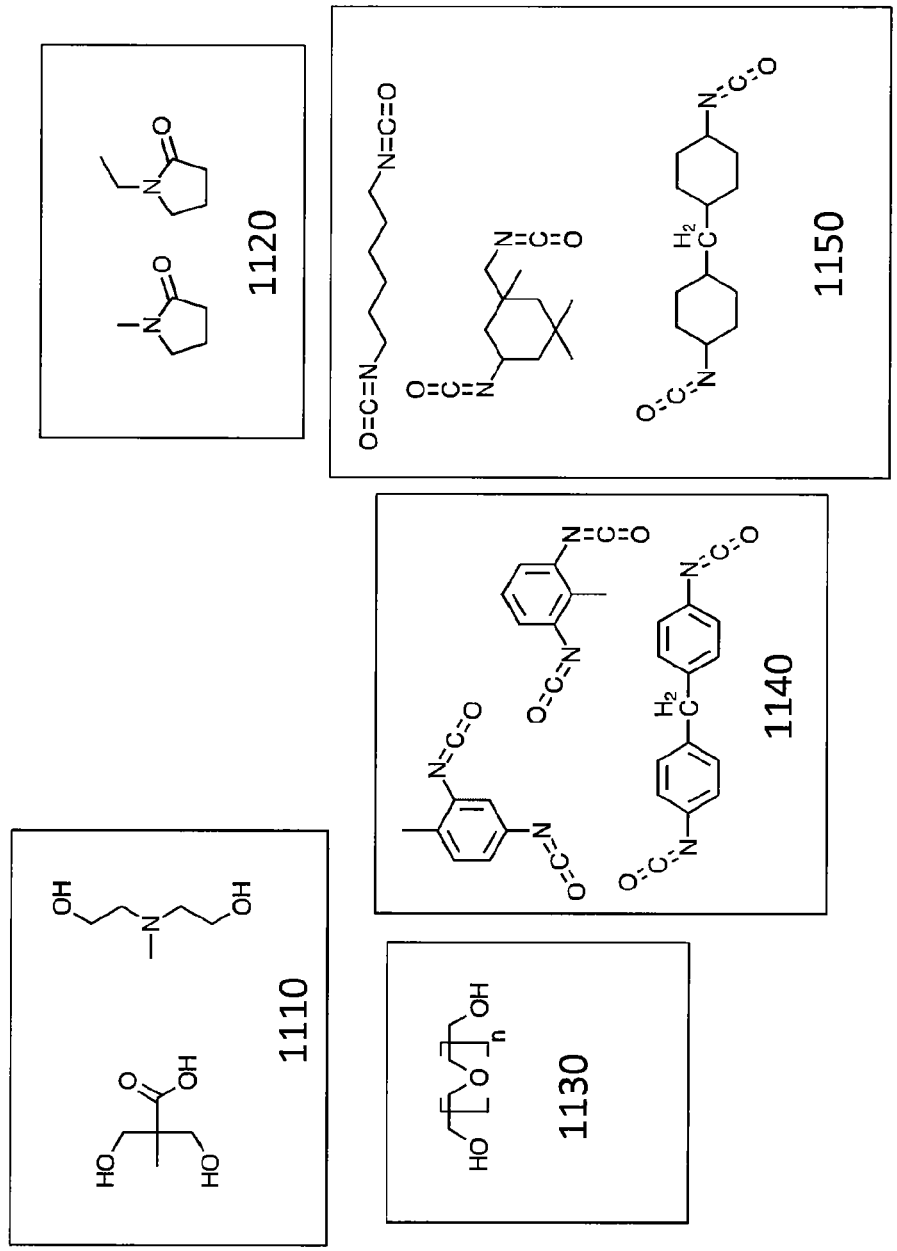
FIG. 14 is a graphical representation of the constituent structures of polyurethane dispersions as known and understood to one skilled in the art of urethane dispersions. Reference numeral 1410 represents structures of ionic species that can be used as internal ions; 1420 represents structures of exemplary coalescing solvents; 1430 represents the structure of non-ionic surfactant that can be used internally or externally; 1440 represents structures of common aromatic polyisocyanates; and 1450 represents structures of common aliphatic polyisocyanates.

The polyisocyanate component of the prepolymer formulations of the presently disclosed and/or claimed inventive concept(s) can be selected from aliphatic polyisocyanates, modified aliphatic polyisocyanates, and mixtures thereof. Examples of aliphatic isocyanate compounds include 1,6-hexamethylene-diisocyanate (HDI), isophorone diisocyanate (IPDI), 2,4- and 2,6-hexahydrotoluene-diisocyanate, 4,4'-, 2,2'- and 2,4'-dicyclohexylmethane diisocyanate (H12MDI), tetramethyl xylene diisocyanate, norbornane diisocyanate, 1,3- and 1,4-(bisisocyanatomethyl)cyclohexane (including cis- or trans-isomers thereof), tetramethylene-1,4-diisocyanate (TMXDI), cyclohexane 1,4-diisocyanate, 4,4'-dicyclohexylmethane diisocyanate, xylene diisocyanate, 1,12-dodecane diisocyanate, 2,2,4-trimethylhexamethylene diisocyanate, and combinations thereof. In one preferred embodiment, the isocyanate component can be selected from 2,4-toluene-diisocyanate, 1,6-toluene-diisocyanate, isophorone diisocyanate (IPDI), and combinations thereof. Mixtures of isocyanates may also be used with the polyurethane dispersions of the presently disclosed and claimed inventive concept(s). For example but not by way of limitation, commercially available mixtures of 2,4- and 2,6-isomers of toluene diisocyanates (TDI) may be used. A "crude" polyisocyanate may also be used in the practice of the presently disclosed and claimed inventive concept(s). For example but not by way of limitation, toluene diisocyanate obtained by the phosgenation of a mixture of toluene diamine isomers or diphenylmethane diisocyanate obtained by the phosgenation of crude methylene diphenylamine may be used as such "crude" polyisocyanates. TDI/MDI blends may also be used and one of ordinary skill in the art would appreciate the advantages of using same (See FIG. 14).

The isocyanate reactive component, referred to herein as the polyol, is comprised of the mixture or blend of the oligomers recovered from the glycolysis of rPET (i.e., the dPET). The polyols used in polyurethane production are those compounds having at least two hydroxyl groups or amine groups. In one aspect of the presently disclosed and/or claimed inventive concept(s), the active hydrogen groups are hydroxyl groups. Representatives of suitable polyols are generally known and are described in such publications as High Polymers, Vol. XVI, "Polyurethanes, Chemistry and Technology" by Saunders and Frisch, Interscience Publishers, New York, Vol. I, pp. 32-42, 44-54 (1962) and Vol. II, pp. 5-6, 198-199 (1964); Organic Polymer Chemistry by K. J. Saunders, Chapman and Hall, London, pp. 323-325 (1973); and Developments in Polyurethanes, Vol. I, J. M. Burst, ed., Applied Science Publishers, pp. 1-76 (1978), the entire contents of each of which are expressly incorporated herein by reference in their entirety.

The polyether polyols of the presently disclosed and/or claimed inventive concept(s) include those obtained by the alkoxylation of suitable starting molecules with an alkylene oxide, such as ethylene oxide (EO), propylene oxide (PO), butylene oxide (BO), or mixtures thereof. Examples of initiator molecules include water, ammonia, aniline or polyhydric alcohols such as dihydric alcohols having a molecular weight of 62-399 g/mol, especially the alkane polyols such as ethylene glycol, propylene glycol, hexamethylene diol, glycerol, trimethylol propane or trimethylol ethane, or the low molecular weight alcohols containing ether groups such as diethylene glycol, triethylene glycol, dipropylene glyol, tripropylene glycol or butylene glycols (See FIG. 14).

In one particular embodiment, the dPET contains greater than 15% GPC chromophore peak area having a molecular weight of >250, greater than 15% GPC chromophore peak area having a molecular weight of >440, greater than 10% GPC chromophore peak area having a molecular weight of >630, greater than 5% GPC chromophore peak area having a molecular weight of >820, greater than 1% GPC chromophore peak area having a molecular weight of >1000, and greater than 0.5% GPC chromophore peak area having a molecular weight of >1200. In an alternative embodiment, the dPET contains greater than 25% GPC chromophore peak area having a molecular weight of >250, greater than 25% GPC chromophore peak area having a molecular weight of >440 or greater, greater than 15% GPC chromophore peak area having a molecular weight of >630, greater than 10% GPC chromophore peak area having a molecular weight of >820, greater than 5% GPC chromophore peak area having a molecular weight of >1000, and greater than 5% GPC chromophore peak area having a molecular weight of >1200. (See FIGS. 4, 5 and 6)

The prepolymers of the presently disclosed and/or claimed inventive concept(s) can be prepared in any way known to one of ordinary skill in the art of preparing polyurethane prepolymers. Often, the polyisocyanate and polyol components are brought together and heated under reaction conditions sufficient to prepare a polyurethane prepolymer, and the stoichiometry of the prepolymer formulations of the presently disclosed and/or claimed inventive concept(s) is such that the polyisocyanate is present in excess. The prepolymer may be made in the presence of a solvent and any solvent remaining in the reaction product mixture may be removed before or after the production of the polyurethane dispersion. In an embodiment, the prepolymers are made in the presence of a non-polar solvent to aid interaction with the dPET. When a solvent is used, examples of solvents which are not reactive with the isocyanate include ketones, such as acetone or methyl-ethyl ketone; ethers such as tetrahydrofuran, dioxane, and dimethoxyethane; and ether esters, such as methoxypropyl acetate. These solvents may be added at any stage of the prepolymer preparation.

Generally, the processes for making polyurethane dispersions are well known in the art. The polymer may be dispersed by a batch or continuous process. When prepared by either method, the resulting dispersion should have a particle size sufficient to provide stability to the dispersion—i.e., the dispersion should not flocculate during storage prior to use in subsequent end products.

The PUDs created within the scope of the presently disclosed and/or claimed inventive concept(s) are internally stabilized. An internally stabilized PUD is one that incorporates ionically or nonionically hydrophilic pendant groups into the polymer backbone particles dispersed into water. (See FIG. 14). Examples of nonionic internally stabilized polyurethane dispersions are described by U.S. Pat. Nos. 3,905,929 and 3,920,598, the entire contents of both of which are herein incorporated by reference. Ionic internally stabilized polyurethane dispersions are described in U.S. Pat. Nos. 6,231,926 and 3,412,054, the entire contents of both of which are herein incorporated by reference in their entirety. Typically, dihydroxyalkylcarboxylic Bronsted-Lowry acids are incorporated into the polyurethane in order to make anionic dispersions. A common monomer used to make an anionic internally stabilized polyurethane dispersion is dimethylolpropionic acid (DMPA). Dihydroxy tertiary amine Lewis bases may be incorporated into the polyurethane in order to promote cationic internal stability. A preferred embodiment of the presently disclosed and/or claimed inventive concept(s) is a PUD comprised of a nonionic group (that does not contain a hydrophilic ionizable group) and a hydrophilic ionizable group (that readily ionizes in water such as DMPA). Other ionizable groups that may be incorporated into the polyurethane include, for example but not by way of limitation, anionic groups such as sulfonic acids and alkali metal salts thereof, and cationic groups including ammonium salts prepared by reaction of a tertiary amine with a strong mineral acid such as phosphoric acid, sulfuric acid, a hydrohalic acid, or a strong organic acid.

Surfactants are deployed into the aqueous phase of the polyurethane dispersion in order to further stabilize the dispersion. The surfactants contemplated for use with the presently disclosed and/or claimed inventive concept(s) include, but are not limited to, cationic, anionic, zwitterionic, or non-ionic surfactants. Examples of anionic surfactants include, but are not limited to, sulfonates, carboxylates, and phosphates. Examples of cationic surfactants include, but are not limited to, quaternary amines. Examples of non-ionic surfactants include, but are not limited to, block copolymers containing ethylene oxide and silicone surfactants, such as ethoxylated alcohol, ethoxylated fatty acid, sorbitan derivative, lanolin derivative, ethoxylated nonyl phenol, or an alkoxylated polysiloxane. As with the ionic groups that may be added to the polyurethane to enhance its dispersibility, as discussed hereinabove, the surfactants can be either external or internal surfactants. External surfactants are not chemically reacted into the polymer during preparation. Internal surfactants are incorporated into the polymer backbone during dispersion preparation (See FIG. 14).

Formation of the prepolymer can take place with or without the use of a catalyst. Suitable catalysts useful for preparing the prepolymer include, but are not limited to, stannous octoate, dibutyl tin dilaurate, and tertiary amine compounds such as triethylamine and bis-(dimethylaminoethyl) ether, morpholine compounds such as ββ'-dimorpholinodiethyl ether, bismuth carboxylates, zinc bismuth carboxylates, iron (III) chloride, potassium octoate, potassium acetate, DABCON® (bicycloamine) (commercially available from Air Products and Chemicals, Inc., Allentown, Pa.), and FASCAT® 2003 (commercially available from Arkema Inc., Philadelphia, Pa.). The amount of catalyst used may be, but not by way of limitation, from about 5 to 200 parts per million of the total weight of prepolymers. In one non-limiting embodiment, a zirconium chelate catalyst such as K-KAT® XC9213 (commercially available from King Industries, Inc., Norwalk, Conn.) is used. Additionally, water degradable catalysts can be used to form the prepolymer. The term "water degradable" means the catalyst deactivates in the presence of water—i.e., the catalyst used in the production of the polyurethane product (which may contain some amount of residual catalyst) is dispersed into the aqueous solvent to thereby create PUD. In this manner, residual catalyst remaining in the PUD, which is thereafter used in a commercial application, does not interfere or react with the resulting PUD coating. Suitable water degradable catalysts include, but are not limited to, zirconium chelate such as the K-KAT® XC9213 catalyst from King Industries, Inc. The amount of water degradable catalyst used can be from about 5 to 200 parts per million. One of ordinary skill in the art would appreciate that any water degradable catalyst for isocyanate reactions could be used.

In one embodiment, the prepolymers are extended with a chain extender to further increase their molecular weight and provide the final PUD with added functionality. Any chain extender known to be useful to those of ordinary skill in the art of preparing polyurethanes can be used with the presently disclosed and/or claimed inventive concept(s). A typical chain extender will have a molecular weight of 30 to 1000 g/mol and have at least two active hydrogen containing groups. Polyamines are a common class of chain extenders, but other materials, particularly water, can function to extend chain length and are contemplated for use. Common chain extenders include, but are not limited to, water, amino ethyl piperazine, 2-methyl piperazine, 1,5-diamino-3-methyl-pentane, isophorone diamine, ethylene diamine, diamino butane, hexamethylene diamine, tetramethylene tetraamine, aminoethyl propyl trimethoxy silane, diethylene triamine, triethylene tetramine, triethylene pentamine, ethanol amine, lysine in any of its stereoisomeric forms and salts thereof, hexane diamine, hydrazine and piperazine.

The prepolymer can be dispersed in an aqueous medium using any method known to those skilled in the art. Typically, the prepolymer is simply added to the aqueous medium with stirring, preferably rapid stirring. Sometimes, high speed/high shear stirring is used to obtain a dispersion of good quality. Typically, the prepolymer and the aqueous medium are combined to provide a polyurethane dispersion. The dispersions will generally have a solids content of from 20 to 60 wt %. Films will not necessarily be prepared from dispersions having this level of solids, as the dispersions themselves may be stored and shipped at a high solids content to minimize shipping costs. As such, the dispersion may be diluted prior to final use.

The prepolymer can be dispersed into the aqueous medium at any temperature. Typically, the temperature is below the boiling point of the aqueous medium. By using a closed reactor capable of withstanding elevated pressure it is possible to disperse the prepolymer in the aqueous medium at a temperature higher than the boiling point of the aqueous medium. Generally, in commercial processes for preparing polyurethane dispersions, the prepolymer is dispersed in the aqueous medium at a temperature of less than about 50° C. and often less than about 25° C. The relatively low temperature is required since the isocyanate groups of the prepolymer undergo a relatively rapid reaction with water that leads to polymerization rendering the prepolymer non-dispersible in water. Furthermore, the rapid reaction of the isocyanate groups of the prepolymer with water, at higher temperatures, leads to the formation of carbon dioxide—thereby resulting in foaming, which renders the process difficult to perform. By lowering the temperature at which the dispersion is formed, such side reactions are reduced. Accordingly, in one non-limiting embodiment, the prepolymer is dispersed in the aqueous medium at a temperature less than about 50° C. In another non-limiting embodiment, the prepolymer is dispersed in the aqueous medium at a temperature ranging from about 20° C. to about 50° C.

The polyurethane dispersions may contain further components and additives for example, but not by way of limitation, inorganic and organic pigments, dyes, leveling agents, viscosity regulators, natural and synthetic waxes, anti-foaming agents, matting agents and others.

The dispersions of the presently disclosed and/or claimed inventive concept(s) are useful in coatings for surfaces, particularly in coatings of metals, glasses, plastics, and cellulosic materials. The coatings based on polyurethane dispersions of the presently disclosed and/or claimed inventive concept(s) have a hardness of 4 H surface scratch hardness, measured 3 days after application. Preferably, the coatings have a hardness of 3 H or greater and, more preferably, have a hardness of 4 H or greater. The PUDs may be applied to the respective substrates by methods such as painting, spraying, flow-coating, transfer-coating, roller coating, brushing, dipping, spreading, curtain coating, and any other coating method now known or developed in the future. The polyurethane dispersions can be pooled on a substrate and then spread over the substrate using a brush or other spreading means. Spraying includes atomizing the PUD and ejecting the atomized material onto the substrate. The PUDs are preferably applied at ambient temperatures. Drying of the products obtained by the various applications of the PUDs can be carried out at room temperature or at elevated temperature.

The oligomeric form of polyethylene terephthalate with hydroxyl and/or amine group(s) (i.e., the dPET) can be reacted with a polyisocyanate to form a polyurethane prepolymer. The polyurethane prepolymer can be formed according to any method known in the art, such as by heating the dPET with hydroxyl and/or amine group(s) with the polyisocyanate until a desired NCO equivalent weight is achieved. Preferably, the polyisocyanate and the dPET are brought together and heated under reaction conditions sufficient to prepare the polyurethane prepolymer. The stoichiometry of the prepolymer formulations, in one embodiment of the presently disclosed and/or claimed inventive concept(s), is such that the polyisocyanate is present in excess. In other embodiments of the presently disclosed and/or claimed inventive concept(s), the stoichiometry of the prepolymer formulations is such that there is an excess or equivalent amount of dPET to polyisocyanate.

Dispersion of the prepolymer in an aqueous solvent to produce the exemplary PUDs of the presently disclosed and/or claimed inventive concept(s) may be generally carried out using a variety of stirring blades (e.g., crescent shaped Teflon stirring blades, Cowles stirring blades, etc.), or other techniques used by a person skilled and trained in the art capable of producing enough shear to disperse. Direct observations indicate that a commercially feasible and stable PUD formulation does not require the aggressive shearing force obtainable through the use of the Cowles blade although it is contemplated for use in the methods of the presently disclosed and/or claimed inventive concept(s). Examples of bench scale and pilot plant scale reactions to produce PUDs of the presently disclosed and/or claimed inventive concept(s) are hereinafter described with particularity.

Figure 15:
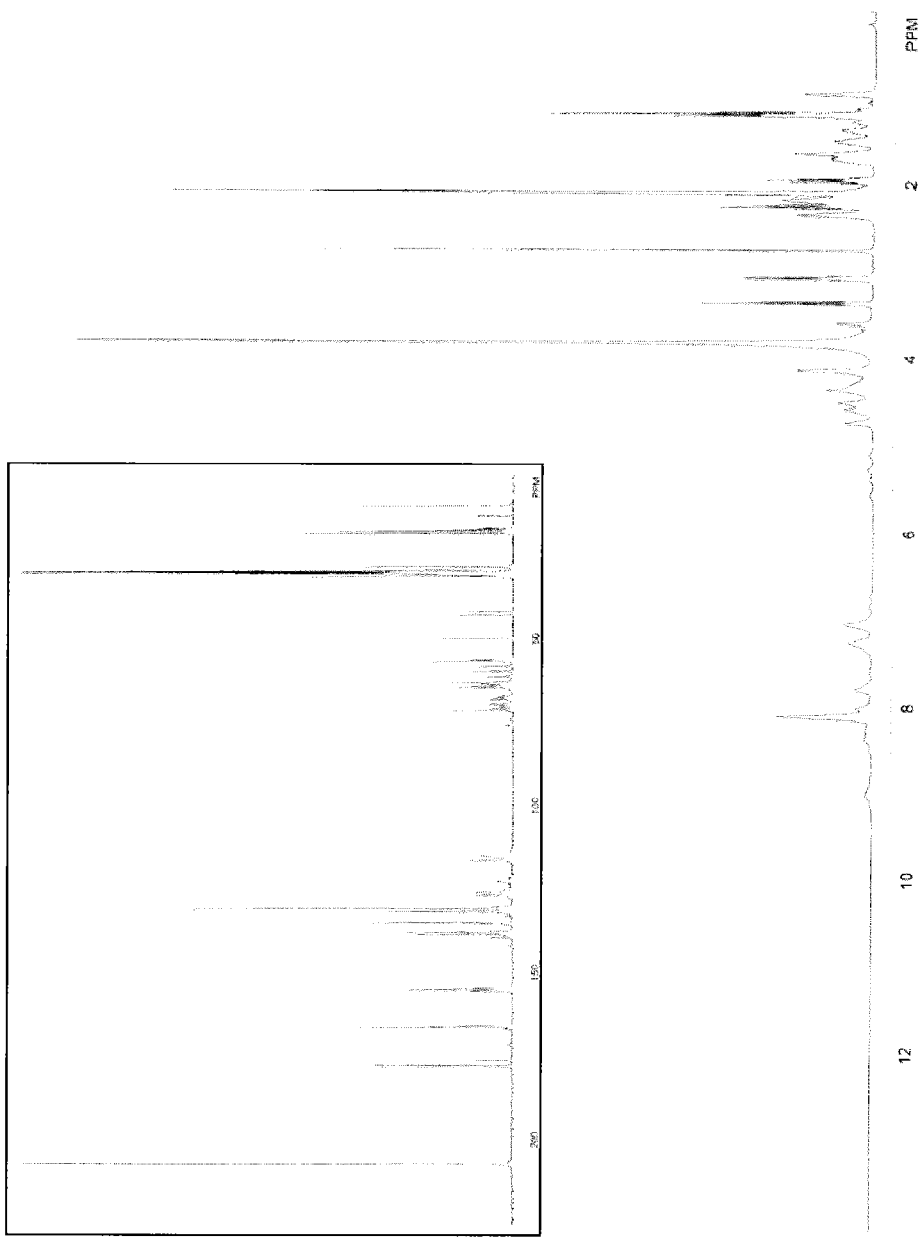
FIG. 15 is a graphical representation of the proton and carbon-13 NMR of a polyurethane dispersion produced according to Example 1.
Figure 16A:
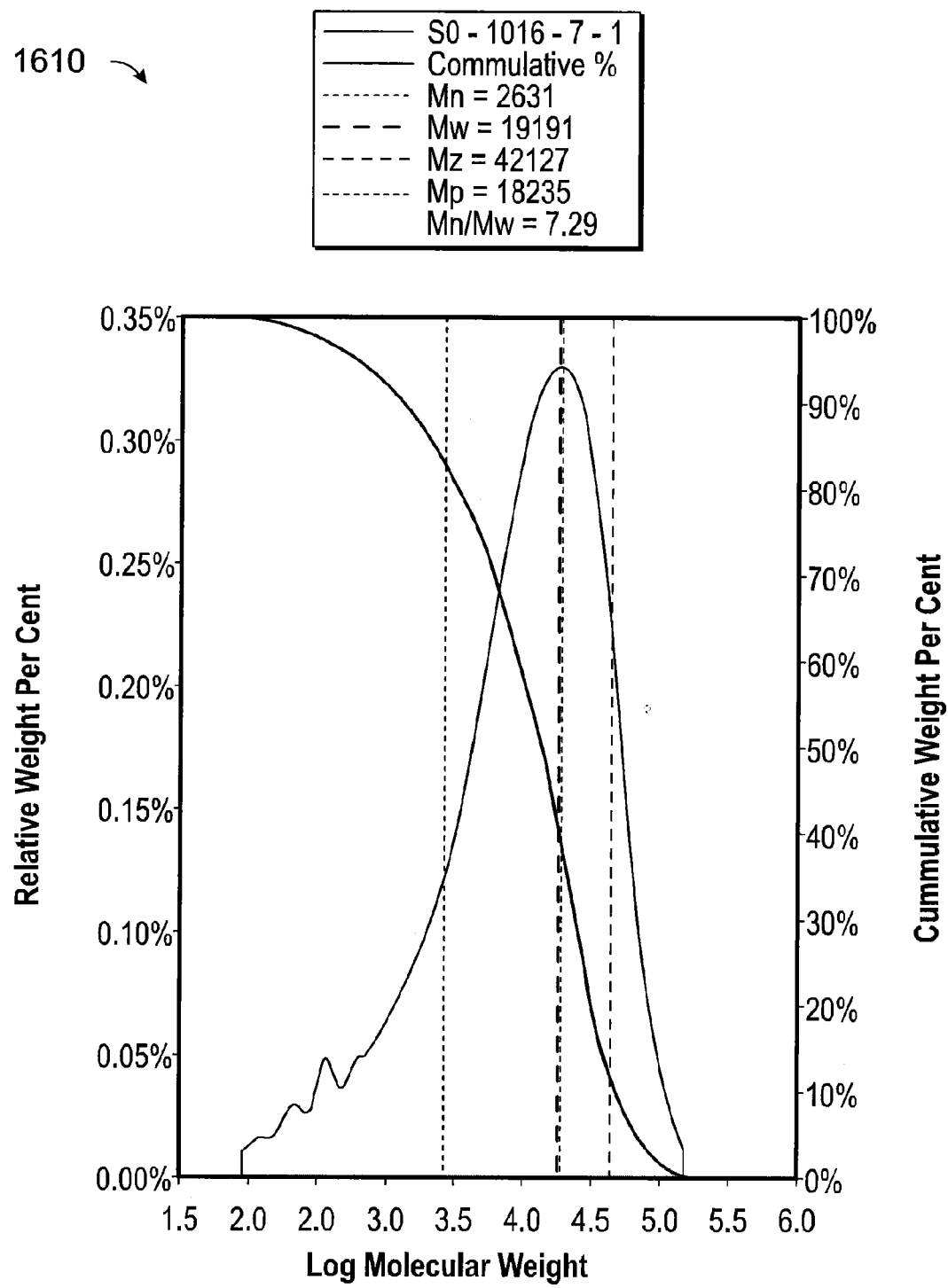
FIG. 16 is a graphical representation of a GPC for two separate runs (16a and 16b) for a polyurethane dispersion produced according to Example 1.
Figure 16B:
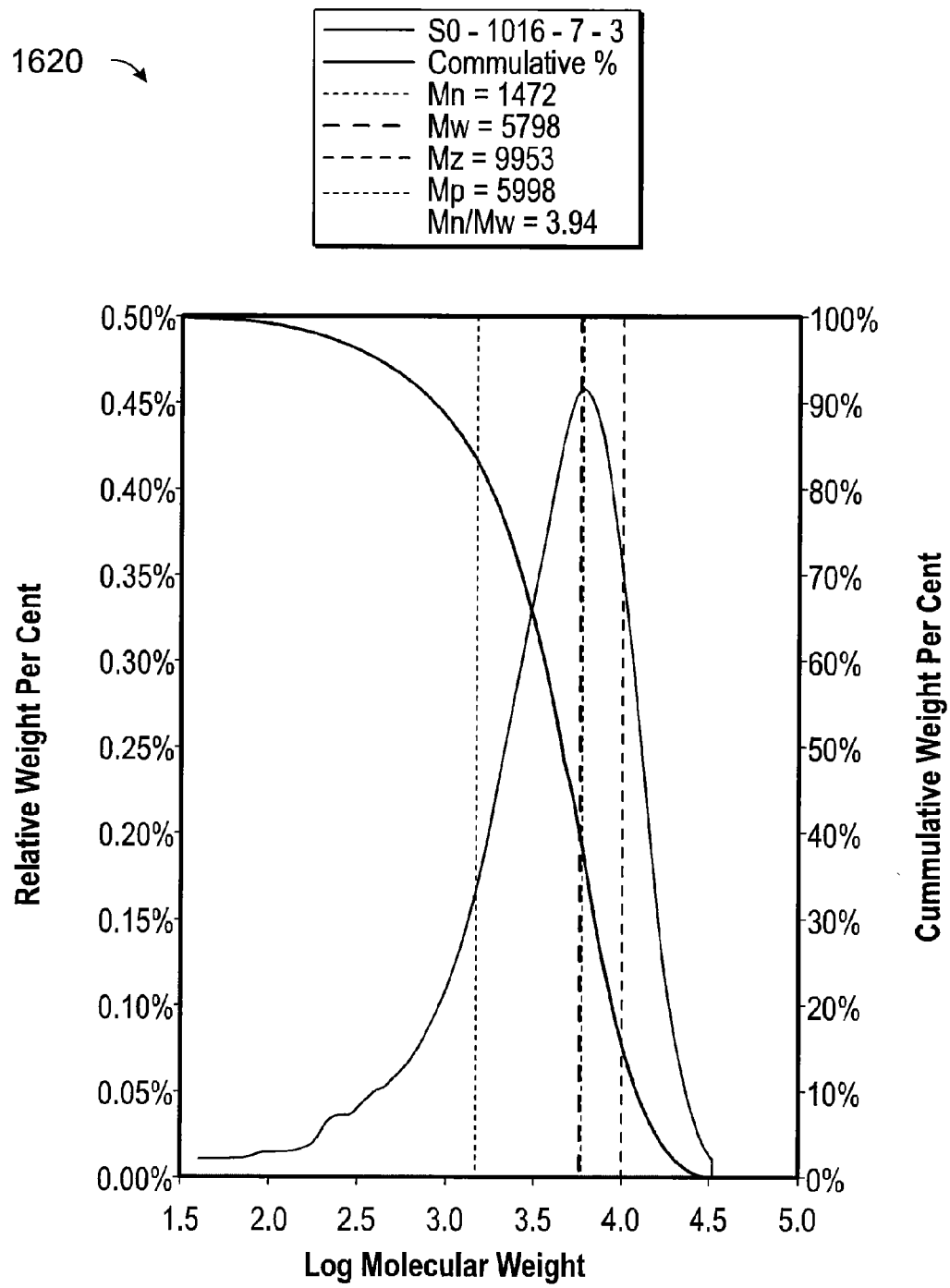
Figure 17:
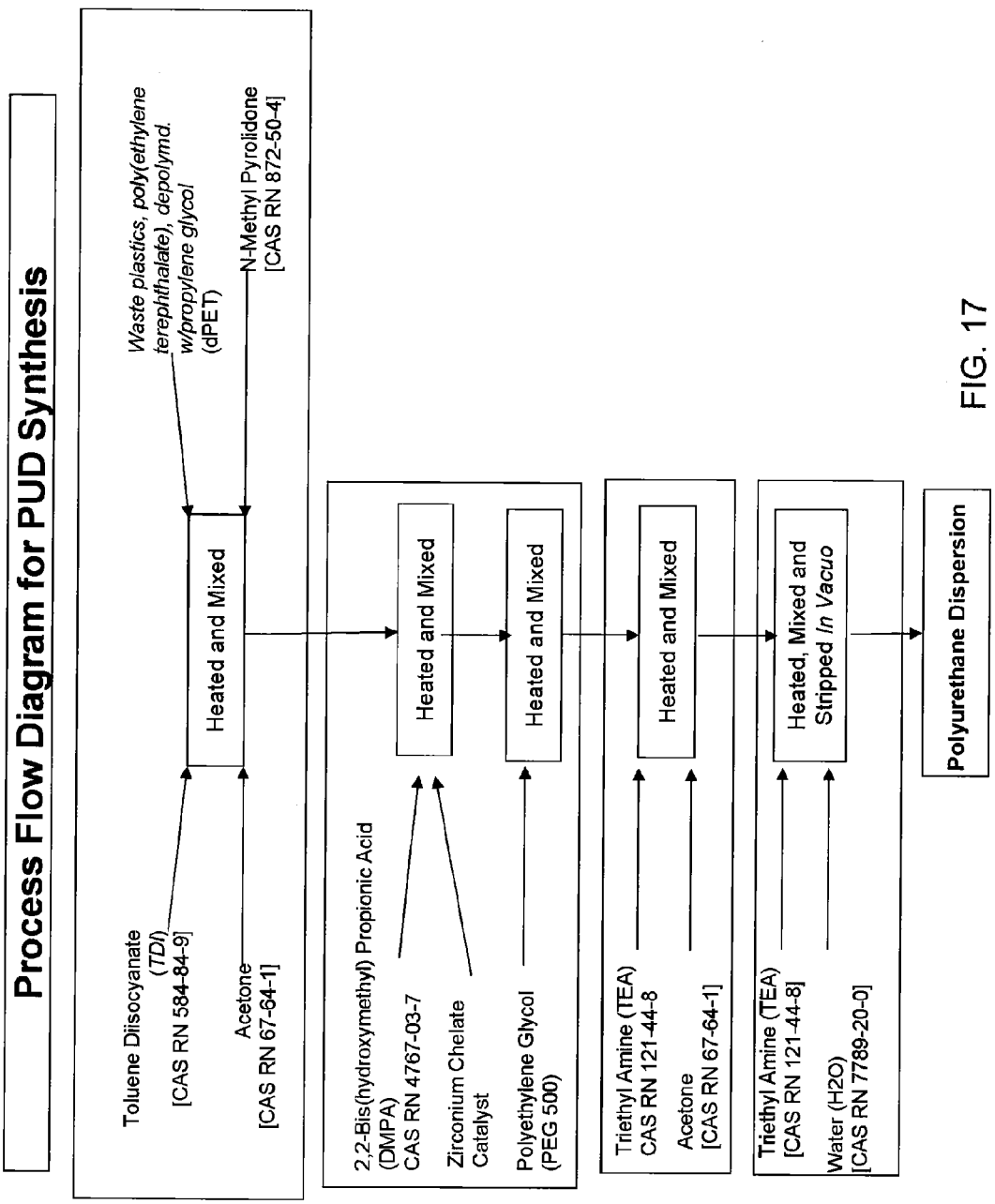
FIG. 17 is a graphical representation of an exemplary process flow diagram for the production of a polyurethane dispersion as described in the examples outlined herein.

The polyurethane dispersions can be further characterized to define the MW and functional connections of the materials of the composition. Examples of such PUDs are displayed in FIGS. 15 and 16. The overall process for the manufacture of PUD lends itself to scalability (FIG. 17), and the process is contemplated as being performed as a batch or continuous process as described, for example but not by way of limitation, in U.S. Pat. No. 7,345,110 and EP Patent No. 2,094,756, the entire contents of both of which are herein incorporated by reference in their entirety. One skilled and trained in the art would appreciate that the processes shown in FIG. 17 are but one example illustrating a production process of manufacturing polyurethane dispersions from PET.

The presently disclosed and/or claimed inventive concept(s) also encompasses a radiation curable composition comprising at least one oligomeric form of polyethylene terephthalate containing hydroxyl and at least one ethylenically unsaturated photopolymerizable compound. In an alternative embodiment, the radiation curable composition comprises a polyurethane resin comprising a reaction product formed by a reaction of a polyisocyanate and at least one oligomeric form of polyethylene terephthalate containing hydroxyl groups and an ethylenically unsaturated photopolymerizable compound. In another embodiment, the radiation curable composition comprises wherein the polyurethane resin comprises a reaction product formed by a reaction of a polyisocyanate, at least one water solubilizing monomer, and at least one oligomeric form of polyethylene terephthalate containing hydroxyl groups. In one embodiment, the composition further comprises water, forming a radiation curable polyurethate dispersion.

The ration curable compositions can be cured by, for example but without limitation, energy in the electromagnetic spectrum including, for example, ultra violet light, electron beams, and other forms of radiant energy. In one embodiment, the radiation curable compositions further comprise photoinitiator, wherein the photoinitiator can be selected from the group consisting of benzoin esters, halomethyl ketones in combination with amines, aromatic ketones in combination with amines, and combinations thereof. In one embodiment, the photoinitiator can be at least one of 2-hydroxy-2-methyl-1-phenyl-propan-1-one and 1-[4-(2-Hydroxyethyoxy)-phenyl]-2-hydroxy-2-methyl-1-propane-1-one.

In one embodiment, the at least one oligomeric form of polyethylene terephthalate containing hydroxyl groups comprises a mixture of reaction products formed by a reaction of polyethylene terephthalate with a glycolysis agent, wherein the at least one oligomeric form of polyethylene terephthalate containing hydroxyl groups comprises a mixture of reaction products formed by a reaction of polyethylene terephthalate with a glycolysis agent. The glycolysis agent can be selected from the group consisting of ethylene glycol, diethylene glycol, propylene glycol, neopentyl glycol, and combinations thereof. In an alternative embodiment, the glycolysis agent is selected from the group consisting of recycled ethylene glycol, recycled diethylene glycol, recycled propylene glycol, recycled neopentyl glycol, and combinations thereof. In one embodiment, a catalyst is used to catalyze the reaction of the polyethylene terephthalate with the glycolysis agent. The can be selected from at least one of zinc acetate and zinc acetate dihydrate.

In one embodiment, the reaction products of the reaction of polyethylene terephthalate with a glycolysis agent can comprise greater than 15% GPC chromophore peak area having a molecular weight of >about 250, greater than 15% GPC chromophore peak area having a molecular weight of >about 440, greater than 10% GPC chromophore peak area having a molecular weight of >about 630, greater than 5% GPC chromophore peak area having a molecular weight of >about 820, greater than 1% GPC chromophore peak area having a molecular weight of >about 1000, and greater than 0.5% GPC chromophore peak area having a molecular weight of >about 1200. In an alternative embodiment, the reaction products of polyethylene terephthalate with a glycolysis agent can comprise greater than 25% GPC chromophore peak area having a molecular weight of >about 250, greater than 25% GPC chromophore peak area having a molecular weight of >about 440, greater than 15% GPC chromophore peak area having a molecular weight of >about 630, greater than 10% GPC chromophore peak area having a molecular weight of >about 820, greater than 5% GPC chromophore peak area having a molecular weight of >about 1000, and greater than 5% GPC chromophore peak area having a molecular weight of >about 1200.

In one embodiment, the polyisocyanate is selected from the group consisting of isophorone diisocyanate (IPDI), methylene bisphenyl isocyanate (MDI), dicyclohexylmethane 4,4'-diisocyanate (H12MDI), cyclohexyl diisocyanate (CHDI), m-tetramethylxylylene diisocyanate (m-TMXDI), tetramethylxylylene diisocyanate (TMXDI), ethylene diisocyanate, 1,2-diisocyanatopropane, 1,3-diisocyanatopropane, 1,6-diisocyanatohexane (hexamethylene diisocyanate or HDI), 1,4-butylene diisocyanate, lysine diisocyanate, 1,4-methylene bis-(cyclohexyl isocyanate), toluene diisocyanate (TDI), m-xylylenediisocyanate (MXDI) and p-xylylenediisocyanate, 4-chloro-1,3-phenylene diisocyanate, 1,5-tetrahydro-naphthalene diisocyanate, 4,4'-dibenzyl diisocyanate, and 1,2,4-benzene triisocyanate, xylylene diisocyanate (XDI), 1,4-diisocyanatobutane, 1,5-diisocyanatopentane, 1,6-diisocyanatohexane, 2-methyl-1,5-diisocyanat-opentane, 1,5-diisocyanato-2,2-di methylpentan e, 2,2,4-trimethyl-1,6-diisoc-yanatohexane, 2,4,4-trimethyl-1,6-diisocyanatohexane, 1,1,0-diisocyanatodecane, 1,3-diisocyanatocyclohexane, 1,4-diisocyanatocyclohexane, 1,3-bis-(isocyanatomethyl)cyclohexane, 1,4-bis-(isocyanatomethyl)cyclohexane, isophorone diisocyanate, 4,4'-diisocyanatodicyclohexylmethane, triisocyanatononane, diisocyanato-1,3-dimethylcyclohexane, 1-isocyanato-1-methyl-3-isocyanatomethylcyclohexane, 1-isocyanato-1-methyl-4-isocyanatomethylcyclohexane, bis -(isocyanatomethyl) norbornane, 1,5-naphthalene diisocyanate, 1,3-bis-(2-isocyanatoprop-2-yl)benzene, 1,4-bis-(2-isocyanatoprop-2-yl)benzene, 2,4-diisocyanatotoluene, 2,6-diisocyanatotoluene, 2,4'-diisocyanatodiphenylmethane, 4,4'-diisocyanatodiphenylmethane, 1,5-diisocyanatonaphthalene, 1,3-bis(isocyanatomethyl)benzene, and combinations thereof.

In one embodiment, the at least one water solubilizing monomer is selected from the group consisting of carboxylates, phosphates, sulf(on)ates, sorbates, poly(ethylene oxide) oligomeric blocks, quaternary amines, and combinations thereof.

In one embodiment, the polyurethane resin comprises a reaction product formed by a reaction of a polyisocyanate, at least one water solubilizing monomer, at least one oligomeric form of polyethylene terephthalate containing hydroxyl groups, and a catalyst. In an alternative embodiment, the radiation curable composition comprises a polyurethane resin comprising a reaction product formed by a reaction of a polyisocyanate, at least one oligomeric form of polyethylene terephthalate containing hydroxyl groups, an ethylenically unsaturated photopolymerizable compound, and a catalyst. In one embodiment, the catalyst is dibutyl tin dilaurate.

The ethylenically unsaturated photopolymerizable compound is selected from the group consisting of methyl methacrylate, ethyl methacrylate, 2-ethylhexyl methacrylate, isobutyl methacrylate, glycidyl methacrylate, glycidyl acrylate, butyl acrylate, 2-hydroxyethyl acrylate, hydroxyethyl(meth)acrylate, 2-methoxyethyl acrylate, 2-phenoxyethyl acrylate, 2-hydroxypropyl acrylate, benzyl acrylate, tetrahydrofurfuryl acrylate, pentaerythritol triacrylate and combinations thereof.

The radiation curable composition can also comprise at least one of a stabilizing compound and an additional polyol. In one embodiment, the stabilizing compound is phenothiazine. In another embodiment, the additional polyol is a natural oil modified polyol which can be for example, but without limitation, Piothane® S-500 (Pioneer Plastics, Auburn, Me.).

The radiation curable compositions as described above can be used in a variety of application for example, but without limitation, as an article of manufacture, a film, a coating, and a adhesive on a variety of substrates including for example, but without limitation, wood, metal, plastics, and other plastics.

The presently disclosed and/or claimed inventive concept(s) also encompasses a method of making a radiation curable composition. In one embodiment, the radiation curable composition is formed by the steps, comprising: (i) adding at least one oligomeric form of polyethylene terephthalate containing hydroxyl groups (as described above) to reactor and optionally adding an additional polyol to the reactor and mixing with the at least one oligomeric form of polyethylene terephthalate containing hydroxyl groups (as described above), (ii) adding at least one ethylenically unsaturated photopolymerizable compound (as described above) to a separate container and optionally adding a stabilizing compound, and thereafter mixing, (iii) mixing the ethylenically unsaturated photopolymerizable compound and the at least one oligomeric form of polyethylene terephthalate containing hydroxyl groups, (iv) heating the reaction mixture, (v) cooling the reaction mixture while adding an isocyanate (as described above), (vi) adding a catalyst to the mixture, (vii) heating the mixture again, (viii) optionally adding at least one additional ethylenically unsaturated photopolymerizable compound. In one embodiment, the mixture was heated to approximately 50° C. in step (iv), and optionally agitated once the mixture softened eventually forming a homogeneous. In one embodiment, the composition is added to water and water solubilizing monomer.

One of ordinary skill in the art would appreciate multiple and varied changes that can be made to these processes and all such changes or variations outside of those clearly defined are encompassed within the present invention. Additionally, one of ordinary skill in the art given the present disclosure, would be capable of making the PUDs described herein and would also appreciate that such PUDs are merely examples and should not be construed as being limiting with respect the variables other than those rigidly defined within the presently disclosed and/or claimed inventive concept(s).

EXAMPLES

The following examples are provided to illustrate the presently disclosed and/or claimed inventive concept(s). The examples are not intended to limit the scope of the presently disclosed and/or claimed inventive concept(s) and should not be so interpreted. All percentages are indicative of weight percent unless otherwise noted. rPET is supplied by Evergreen Plastics, and all other chemical reactants were obtained from Sigma-Aldrich unless otherwise noted. The following dPET Examples A-G were carried out under the assumption that the PET repeat unit had a molecular weight of about 192 g/mol. Additionally, dPET Examples A-D were carried out as bench scale reactions as described below without removing byproducts during the reaction. dPET Example E was carried out as a large scale reaction intended to simulate industrial conditions, described below, wherein with the above-described byproducts were removed during the reaction. dPET Example F was carried out as described below in a similar large scale reaction but without the removal of byproducts. Additionally, Examples 1-10 disclose experimental methods for making polyurethane dispersions using dPETs A-E, Examples 11-18 disclose methods of making UV curable urethane acrylates and coatings thereof, and Examples 19-22 disclose methods of making UV curable polyethylene terephthalates and coatings thereof.

dPET Example A rPET was depolymerized by using 0.9Eq of propylene glycol in the presence of 1.5 mol % of zinc acetate dihydrate and heated to >180-210° C. for 10 hours or until the reaction mixture became uniphasic in an open vessel equipped with a reflux condenser. Upon completion of the reaction, the mixture was cooled to 120° C. and filtered to remove any coarse particle impurities or unreacted PET. The reaction mixture was then allowed to cool to room temperature for characterization and further reaction.

dPET Example B rPET was depolymerized by using 0.8Eq of propylene glycol in the presence of 1.5 mol % of zinc acetate dihydrate and heated to >180-210° C. for 12 hours or until the reaction mixture became uniphasic in a closed vessel. Upon completion of the reaction, the mixture was cooled to 120° C. and filtered to remove any coarse particle impurities or unreacted PET. The reaction mixture was then allowed to cool to room temperature for characterization and further reaction.

dPET Example C rPET was depolymerized by using 1.2Eq of propylene glycol in the presence of 1.5 mol % of zinc acetate dihydrate and heated to >180-210° C. for 12 hours or until the reaction mixture became uniphasic in a closed vessel. Upon completion of the reaction, the mixture was cooled to 120° C. and filtered to remove any coarse particle impurities or unreacted PET. The reaction mixture was then allowed to cool to room temperature for characterization and further reaction.

dPET Example D rPET was depolymerized by using 399.4 lbs of neopentyl glycol in the presence of 11.93 lbs of zinc acetate dihydrate and heated to >180-210° C. for 8 hours or until the reaction mixture became uniphasic in a closed vessel. Upon completion of the reaction the mixture, was cooled to 120° C. and filtered to remove any coarse particle impurities or unreacted PET. The reaction mixture was then allowed to cool to room temperature for characterization and further reaction.

dPET Example E rPET was depolymerized using the process illustrated in FIG. 11 and described in detail above under the heading "Process of Digesting rPET with the Removal of Byproducts During the Reaction." 2,593 lbs. of propylene glycol and 139 lbs. of zinc acetate dihydrate were added to a continuous stir tank reactor. The mixture was heated then agitated until the propylene glycol and zinc acetate dihydrate reached a homogenized state. After reaching homogenization, the agitation was stopped and 7,268 lbs. of PET (recycled/virgin and/or pellet/flake) was added to the reactor. The reaction was then heated by setting the riser pipe (1106 in FIG. 11) to full cooling. Once the reactor temperature plateaued, the temperature on the riser pipe was increased to a range of about 95-100° C. These conditions were maintained until distillate production waned and the reactor temperature held steady. Then, the riser pipe temperature was increased to a range of about 105-110° C., which caused the reactor temperature to rise above 185° C. The reaction was allowed to continue at temperatures above 185° C. until there were no visible signs of PET particle(s) in the reaction mixture and more than 600 g of distillate per 100 lbs. of reaction mixture were collected. During the reaction, a biphasic distillate was observed and collected comprising a dense colorless clear phase and a less dense yellow tinted clear phase having nearly equal volumes. The biphasic distillate was analyzed to avoid excess glycol removal and ensure the sufficient removal of the byproduct to avoid compromising the quality of the dPET product. The dPET product was then filtered through a coarse woven filter having an opening diameter of about 55 μm or greater. The resulting filtrate was then transferred to another tank reactor for subsequent reactions.

dPET Example F

PET was depolymerized using the process illustrated in FIG. 11 without the removal of byproducts described in Example E. Here, 2,593 lbs. of propylene glycol and 139 lbs. of zinc acetate dihydrate were added to a continuous stir tank reactor. The mixture was heated then agitated until the propylene glycol and zinc acetate dihydrate reached a homogenized state. After reaching homogenization, the agitation was stopped and 7,268 lbs. of PET (recycled/virgin and/or pellet/flake) was added to the reactor. The reaction was then heated by setting the riser pipe (1106 in FIG. 11) to full cooling. Once the reaction temperature plateaued, the temperature on the riser pipe was maintained and the reactor temperature was in increased to 195-205° C. These conditions were maintained, however visible signs of PET particle(s) in the reaction mixture persisted. The dPET product was then filtered through a coarse woven filter having an opening diameter of about 55 μm or greater. The product obtained was not useable as it contained substantial amounts of PET that was undigested.

Examples of Polyurethane Dispersions Using dPET Examples A-E

Example 1

Product from dPET Example A was used in the following: 67.7 g of toluene diisocyanate (TDI) and 20 mL of N-methylpyrrolidone (NMP) were heated to 60° C. forming a TDI/NMP solution. A solution of 1% dibutyltin dilaurate in NMP (3 drops) was added to the TDI/NMP solution. A mixture comprising 60.4 g of dPET and 13.1 g of 2,2 bis(hydroxymethyl)propionic acid (DMPA in 20 mL of NMP was heated to 100° C. and slowly added to the TDI/NMP solution. A water bath was used to maintain the temperature at about 50-70° C. and an additional 10 mL NMP was used to complete the transfer. After stirring for 45 min. at about 55° C., a solution of PEG-2000 in about 50 mL of acetone was added. An additional charge of 1% dibutyltin dilaurate in NMP (3 drops) was added. The solution was stirred for 30 min at about 55° C. 18 mL of triethylamine was then added. The reaction mixture was stirred with 400 mL deionized water and acetone was removed on a rotary evaporator under vacuum. The resulting polyurethane dispersion was a green solution with a slight amount of haze.

Example 2

Product from dPET Example B was used in the following: 50 g of dPET and 207.5 mL acetone were mixed in a water bath to form a dPET/acetone solution. In a 1 L 4-neck round bottom flask fitted with a mechanical stirrer, thermocouple, and condenser under $N_2$, 72.6 g of toluene diisocyanate and 75.8 g of NMP were added. 137.5 mL of acetone was then added. Thereafter, 23.13 g of 2,2 bis(hydroxymethyl)propionic acid (DMPA) was added as the temperature was raised from ambient temperature to about 30° C. Approximately 15 drops of a solution of 4% zirconium (IV) acetylacetonate in NMP was then added at about 35° C. At about 40° C., the dPET/acetone solution was added in the flask. The temperature was raised to about 55° C. 4.67 grams sample were withdrawn and the NCO was measured as about 156.8 mmoles. After stirring for about three hours at 55° C., 11.93 g glycerin and 15 drops of the 4% zirconium (IV) acetylacetonate in NMP solution were added. The solution was stirred for about one hour at 55° C. Then, 27.5 g triethylamine was added. The reaction mixture was stirred with 250 g deionized water and acetone was removed on a rotary evaporator under vacuum. The resulting polyurethane dispersion was a clear gold solution.

Example 3

Product from dPET Example C was used in the following: 39 g of dPET and 150 mL of acetone were mixed in a water bath to form a dPET/acetone solution. In a 1 L 4-neck round bottom flask fitted with a mechanical stirrer, thermocouple, and condenser under $N_2$, 87.06 g of toluene diisocyanate, 90.99 g of N-methylpyrrolidone (NMP), and 100 mL of acetone were added. Then, 27 g of 2,2 bis(hydroxymethyl)propionic acid (DMPA) was added as the temperature was raised from ambient to about 50° C. At about 50° C., the dPET/acetone solution was added in the flask. 8 drops of a solution of 4% zirconium (IV) acetylacetonate in NMP was then added at about 35° C. The temperature was raised to about 55° C. After stirring for about 2.5 hours at 55° C., a 2.48 g sample was withdrawn and the NCO was measured at about 265 mmoles. Then, 15.3 g ethylene glycol and 18 drops of the 4% zirconium (IV) acetylacetonate in NMP solution were added. The resulting solution was stirred for about one hour at 55° C. Then, 33 g of triethylamine was added. The reaction mixture was stirred with 300 g deionized water and acetone was removed on a rotary evaporator under vacuum. The resulting polyurethane dispersion was a clear gold solution.

Example 4

Product from dPET Example A was used in the following: 83.03 g of dPET, 102.06 g of acetone, and 31.29 g of N-methylpyrrolidone (NMP) were mixed at room temperature. In a 500 mL 1-neck round bottom flask equipped with a magnetic stirrer, hot plate, and condenser, 80.04 g of toluene diisocyanate and the dPET/acetone/NMP mixture were added under nitrogen at room temperature. The temperature was raised to about 50° C. Two drops of K-KAT®XC-9213 (zirconium chelate catalyst, King Industries Inc., Norwalk, Conn.) were added. The mixture was heated to about 50° C. for around one hour at reflux. A pot sample was withdrawn for NCO titration to determine whether the reaction was complete. The NCO value was measured less than 395.8 mmoles and then 46.06 grams n-methyldiethanolamine (NMDEA) was added. The mixture was heated to reflux for about one hour. A pot sample was withdrawn for NCO titration and the NCO value was less than 376.0 mmoles. 33.76 grams propionic acid was then added. 249 g DI water was added for dispersion. Acetone was removed on a rotary evaporator under vacuum. The average solid weight percentage in the resulting PUD was about 34.03 wt %.

Example 5

Product from dPET Example B was used in the following: 80.98 g dPET, 105.58 g acetone, and 29.58 g N-methylpyrrolidone (NMP) were mixed at room temperature. In a 500 mL 1-neck round bottom flask equipped with a magnetic stirrer, hot plate and condenser, 80.01 g of toluene diisocyanate and the above dPET/acetone/NMP mixture were added at room temperature under nitrogen. The temperature was then raised to about 55° C. Then, two drops of K-KAT®XC-9213 (zirconium chelate catalyst, King Industries Inc., Norwalk, Conn.) were added. The mixture was heated to about 50° C. for about one hour at reflux. A pot sample was withdrawn for NCO titration to determine whether the reaction was complete. The NCO value was determined to be less than about 384.1 mmoles. 46.06 g of n-methyldiethanolamine NMDEA was then added. The mixture was heated to reflux for about one hour. A pot sample was withdrawn for NCO titration and the NCO value was determined to be less than 366.7 mmoles. Thereafter, 29.76 g of propionic acid was added, followed by the addition of 249 g of DI water for dispersion. Acetone was removed on a rotary evaporator under vacuum. The average solid weight percentage in the resulting PUD was about 34.03 wt %.

Example 6

Product from dPET Example C was used in the following: 83.5 g dPET and 95 mL acetone were mixed in a water bath at about 35-40° C. to form a dPET/acetone solution. In a 1 L 4-neck round bottom flask fitted with a mechanical stirrer, thermocouple, and condenser under $N_2$, 80 g of toluene diisocyanate (TDI), 95 mL of acetone, and 29.5 mL of N-methylpyrrolidone (NMP) were added together to form a TDI/actone/NMP solution. Approximately 0.03 g of a solution of 4% zirconium (IV) acetylacetonate in NMP was then added to the TDI/acetone/NMP solution at room temperature. Thereafter, the dPET/acetone solution was added in the TDI/acetone/NMP solution and the temperature was increased to about 40° C. 4.45 g sample was withdrawn and the NCO was measured to be about 342.3 mmoles. 46 g of N-methyldietheanolamine (NMDEA)) was then added. The temperature was increased to about 50° C. An additional 0.03 g of the 4% zirconium (IV) acetylacetonate in NMP solution was then added at 50° C. After about one hour, a 4.52 g sample was withdrawn and the NCO was about 416.5 mmoles. 28.59 g propionic acid was then added. The reaction mixture was stirred with 500 g deionized water. Acetone was removed on a rotary evaporator under vacuum. The resulting PUD was a clear gold solution.

Example 7

Product from dPET Example A was used in the following: 562.5 g of dPET from Example A, 315.15 g of a secondary polylol (MW=2000), 227.56 g of N-methylpyrrolidinone, and 802.13 g acetone were transferred to a 5000 mL reactor kettle and heated to 40° C. to solubilize the dPET. This was performed under a nitrogen purge, which continued for duration of the reaction. While stirring, 750 g of tolylene diisocyanate were added to the polyol solution. After stirring for 60 min. at about 60° C., 150 g of 2,2-bis(hydroxymethyl) propionic acid were washed in with an amount of acetone. The reaction was then catalyzed by addition of 0.23 g of K-KAT®XC-9213 (King Industries Inc., Norwalk, Conn.). After stirring for two and a half hours at about 60° C., 15 g of polyethylene glycol (MW 4000) were added. After this hold period, 315 g of triethylamine were added. The resulting prepolymer was then dispersed into deionized water, made alkaline with triethylamine. The acetone and an amount of water were then removed by rotary evaporation in vacuum.

Example 8

Product from dPET Example A was used in the following: 701 g of dPET Example A, 282.9 g of N-methylpyrrolidinone, and 835 g of acetone were transferred to a 5000 mL reactor kettle and heated to 40° C. to solubilize the dPET. This was performed under a nitrogen purge, which continued for duration of the reaction. While stirring, 632.9 g of tolylene diisocyanate were added to the polyol solution. The reaction was then catalyzed by addition of 1.12 g of K-KAT®XC-9213 (King Industries Inc., Norwalk, Conn.). After stirring for 60 min at about 60° C., 28.68 g of polyethylene glycol (MW 4000) were washed in with the balance of acetone. After stirring for two and a half hours at about 60° C., 214 g of N-methyldiethanolamine were added. After an hour hold period, 304 g of propionic acid were added. The resulting prepolymer was then dispersed into 7600 g of deionized water and made acidified with 152 g of propionic acid. The acetone and an amount of water were then removed by rotary evaporation in vacuum.

Example 9

Product from dPET Example E was used in the following: 214 lbs of dPET from Example E, 119 lbs of a secondary polyol (MW=2000), 86 lbs of N-methylpyrrolidinone, and 625 lbs acetone were transferred to a properly sized continuous stir tank reactor and heated to 40° C. to solubilize the dPET. This was performed under a nitrogen purge, which continued for duration of the reaction. While stirring, 284 lbs of tolylene diisocyanate were added to the polyol solution. After stirring for 60 min. at about 60° C., 57 lbs of 2,2-bis(hydroxymethyl)propionic acid were washed in with an amount of acetone. The reaction was then catalyzed by addition of 0.17 lbs of K-KAT®XC-9213 (King Industries Inc., Norwalk, Conn.). After stirring for two and a half hours at about 60° C., 5.69 lbs of polyethylene glycol (MW 4000) were added. After this hold period, 119 lbs of triethylamine were added. The resulting prepolymer was then dispersed into deionized water, made alkaline with triethylamine. The acetone and an amount of water were then removed by rotary evaporation in vacuum.

Example 10

Product from dPET Example D was used in the following: 112.91 lbs. (11.16 gallons) of toluene diisocyanate was charged into an appropriately sized continuous stir tank reactor along with 160 lbs. of reagent grade acetone. 22.12 lbs. of 1-methyl-2-pyrrolidinone (NMP) was then added to the reactor in addition to 21.65 lbs. (2.59 gallons) of 2,2 bis(hydroxymethyl)propionic acid (DMPA), 0.0763 lbs. (0.0089 gallons; 35.02 grams) of 1% dibutyltin dilaurate in NMP, and 106.74 lbs. (16.0 gallons) of dPET from Example D. 20 lb (3 gallons) of reagent grade acetone and 17.12 (2 gallons) of NMP were then added to the reaction mixture and stirred at 50° C. for a time to sufficiently react the isocyanate, as verified by analytical titration. 13.6 lb. PEG 200 was then charged to 0.0763 lb (35.02 grams) of 1% dibutyltin dilaurate/NMP solution with 64.3 lbs (9.74 gallons) of reagent grade acetone. The resulting reaction mixture was stirred at 55° C. for 60 minutes. A reaction sample was taken and titrated to obtain the isocyanate content. If the reaction was not complete, the reaction was allowed to proceed while sampling every 30 minutes until complete. Once the reaction was determined to be completed, the reaction mixture was cooled to 40 to 50° C., and thereafter 16.32 lbs. (2.70 gallons) of triethylamine (TEA) was added to the reactor. The temperature was maintained in the range of about 40 to 50° C. during TEA addition. 650 lbs. of water was then charged to a dispersion vessel fitted for high shear agitation and heated to 40° C. while being stirred. Under nitrogen pressure, the reaction mixture was transferred to the dispersion vessel. Approximately, 95-98% of the acetone was removed from the reaction mixture by vacuum distillation at 25-30° C. The resulting PUD was then packaged into appropriate containers through 100 micron filter bags. Examples of UV Curable Polyurethane Dispersions Using dPET:

The apparatus for Examples 11 to 18 directed to the preparation of urethane acrylates from polyurethane dispersions consisted of (i) a reaction vessel with an overhead mixer, stir bearing, stir shaft, and stir blade for agitation during the reaction, (ii) a water condenser, (iii) a thermal probe, and (iv) a source of dry nitrogen.

Example 11

Initially, 46.4 g dPET from Example A and 17.0 g Piothane® S-500 (a natural oil based polyol from Panolam Industries International, Inc., (Shelton, Conn.)) were added into the reaction vessel. In a separate container, tetrahydrofurfuryl acrylate (80.0 g) and phenothiazine (0.16 g) were premixed. Once the phenothiazine was fully dissolved in the tetrahydrofurfuryl acrylate, the solution was added to the reaction vessel forming a reaction mixture. The reaction mixture was then heated to approximately 50° C. and agitated once the mixture softened eventually forming a homogeneous mixture. The reaction mixture was then removed from heat source and allowed to cool to 25° C. while adding isophorone diisocyanate (125.0 g) making sure the reactor contents did not exceed 65° C. Once the temperature stabilized, 0.6 g dibutyltin dilaurate catalyst was added to the reaction mixture. Thereafter, the reaction mixture was again heated to a target temperature of 50° C. and allowed to remain at 50° C. while stirring for approximately one hour. Keeping the reaction mixture at 50° C., 9.5 g of dimethylolpropionic acid was then added to the reaction mixture and allowed to remain at 50° C. while stirring until the reaction reached completion. Thereafter, 38.75 g of pentaerythritol triacrylate was added to the reaction mixture while keeping the reaction mixture at 50° C. (while stirring) until the reaction was complete. Lastly, 7.2 g of triethylamine (TEA) was mixed thoroughly with the reaction mixture which was thereafter allowed to cool to ambient temperature, as a polyurethane acrylate.

A separate dispersion vessel was then prepared comprising approximately 540.4 g water and about 11.0 g ethylenediamine (EDA). The urethane acrylate, as described above, was then dispersed in the separate dispersion vessel at an appropriate rate and shear to ensure sustainably suspended and dispersed particles, thereby forming a UV curable polyurethane dispersion. The UV curable polyurethane dispersion was observed to be a continuous phase with a slight haze. The UV curable polyurethane dispersion was then coated onto a substrate and UV-cured using one of the methods described below. After which, various physical properties of the UV cured coating were tested using several of the testing procedures outlined below.

Example 12

Initially, 46.4 g dPET from Example A and 17.0 g Piothane® S-500 (a natural oil based polyol from Panolam Industries International, Inc., (Shelton, Conn.)) were added into the reaction vessel. In a separate container, tetrahydrofurfuryl acrylate (80.0 g) and phenothiazine (0.16 g) were premixed. Once the phenothiazine was fully dissolved in the tetrahydrofurfuryl acrylate, the solution was added to the reaction vessel forming a reaction mixture. The reaction mixture was then heated to approximately 50° C. and agitated once the mixture softened eventually forming a homogeneous mixture. The reaction mixture was then removed from heat source and allowed to cool to 25° C. while adding isophorone diisocyanate (125.0 g) making sure the reactor contents did not exceed 65° C. Once the temperature stabilized, 0.6 g dibutyltin dilaurate catalyst was added to the reaction mixture. Thereafter, the reaction mixture was again heated to a target temperature of 50° C. and allowed to remain at 50° C. while stirring for approximately one hour. Keeping the reaction mixture at 50° C., 9.5 g of dimethylolpropionic acid was then added to the reaction mixture and allowed to remain at 50° C. while stirring until the reaction reached completion. Thereafter, 38.75 g of pentaerythritol triacrylate was added to the reaction mixture while keeping the reaction mixture at 50° C. (while stirring) until the reaction was complete. Lastly, 7.2 g of triethylamine (TEA) was mixed thoroughly with the reaction mixture which was thereafter allowed to cool to ambient temperature, as urethane acrylate.

A separate dispersion vessel was then prepared comprising approximately 469.4 g water and about 10.0 g ethylenediamine (EDA). The urethane acrylate, as described above, was then dispersed in the separate dispersion vessel at an appropriate rate and shear to ensure sustainably suspended and dispersed particles, thereby forming a UV curable polyurethane dispersion. The UV curable polyurethane dispersion was observed to be a continuous phase with a slight haze. The UV curable polyurethane dispersion was then coated onto a substrate and UV-cured using one of the methods described below. After which, various physical properties of the UV cured coating were tested using several of the testing procedures outlined below.

Examples of Polyurethane Acrylates Using dPET:

Example 13

Initially, 46.4 g dPET from Example E and 17 g Piothane® S-500 (a natural oil based polyol from Panolam Industries International, Inc., (Shelton, Conn.)) were added into the reaction vessel. In a separate container, 80 g tetrahydrofurfuryl acrylate (Sartomer® SR285 from Sartomer Company (Exton, Pa.)) and 0.16 g phenothiazine were premixed to form a homogeneous solution. Once the phenothiazine was fully dissolved in the tetrahydrofurfuryl acrylate, the solution was added to the reaction vessel forming a reaction mixture. The reaction mixture was then heated to approximately 50° C. and agitated once the mixture softened eventually forming a homogeneous mixture. The reaction mixture was then removed from heat source and allowed to cool to 25° C. while adding isophorone diisocyanate (125 g) drop wise over the course of approximately 2 minutes making sure the reactor contents did not exceed 65° C. Once the temperature stabilized around 25° C., 0.6 g dibutyltin dilaurate catalyst was added to the reaction mixture. Thereafter, once the temperature again stabilized, the reaction mixture was heated to a target temperature of 50° C. and allowed to remain at 50° C. while stirring for approximately one hour. Thereafter, 67.25 g of pentaerythritol triacrylate was added to the reaction mixture over a course of one minute, where after the temperature of the reaction mixture was maintained at 50° C. (while stirring) for approximately 3 hours. Afterwards, 66.66 g of hydroxyethyl methacrylate as added and allowed to react for an additional 1.5 hours. Then, the reaction mixture was poured into a container and allowed to cool to ambient temperature, as a urethane acrylate. The urethane acrylate was then coated onto a substrate and UV-cured using one of the methods described below. After which, various physical properties of the UV cured coating were tested using several of the testing procedures outlined below.

Example 14

Initially, 46.4 g dPET from Example E and 17.0 g Piothane® S-500 (a natural oil based polyol from Panolam Industries International, Inc., (Shelton, Conn.)) were added into the reaction vessel. In a separate container, 80.0 g tetrahydrofurfuryl acrylate (Sartomer® SR285 from Sartomer Company (Exton, Pa.)) and 0.16 g phenothiazine were premixed to form a homogeneous solution. Once the phenothiazine was fully dissolved in the tetrahydrofurfuryl acrylate, the solution was added to the reaction vessel forming a reaction mixture. The reaction mixture was then heated to approximately 50° C. and agitated once the mixture softened eventually forming a homogeneous mixture. The reaction mixture was then removed from heat source and allowed to cool to 25° C. while adding hexamethylene diisocyanate (94.58 g) drop wise over the course of approximately 2 minutes making sure the reactor contents did not exceed 65° C. Once the temperature stabilized around 25° C., 0.6 g dibutyltin dilaurate catalyst was added to the reaction mixture. Thereafter, once the temperature again stabilized, the reaction mixture was heated to a target temperature of 50° C. and allowed to remain at 50° C. while stirring for approximately one hour. Thereafter, 48.83 g of pentaerythritol triacrylate was added to the reaction mixture over a course of one minute, where after the temperature of the reaction mixture was maintained at 50° C. (while stirring) for approximately 3 hours. Afterwards, 74.70 g of hydroxyethyl methacrylate as added and allowed to react for an additional 1.5 hours. Then, the reaction mixture was poured into a container and allowed to cool to ambient temperature, as a urethane acrylate. The urethane acrylate was then coated onto a substrate and UV-cured using one of the methods described below. After which, various physical properties of the UV cured coating were tested using several of the testing procedures outlined below.

Example 15

Initially, 46.4 g dPET from Example E and 17 g Piothane® S-500 (a natural oil based polyol from Panolam Industries International, Inc., (Shelton, Conn.)) were added into the reaction vessel. In a separate container, 71.3 g tetrahydrofurfuryl acrylate (Sartomer® SR285 from Sartomer Company (Exton, Pa.)) and 0.14 g phenothiazine were premixed to form a homogeneous solution. Once the phenothiazine was fully dissolved in the tetrahydrofurfuryl acrylate, the solution was added to the reaction vessel forming a reaction mixture. The reaction mixture was then heated to approximately 50° C. and agitated once the mixture softened eventually forming a homogeneous mixture. The reaction mixture was then removed from heat source and allowed to cool to 25° C. while adding isophorone diisocyanate (125 g) drop wise over the course of approximately 2 minutes making sure the reactor contents did not exceed 65° C. Once the temperature stabilized around 25° C., 0.6 g dibutyltin dilaurate catalyst was added to the reaction mixture. Thereafter, once the temperature again stabilized, the reaction mixture was heated to a target temperature of 50° C. and allowed to remain at 50° C. while stirring for approximately one hour. Thereafter, 96 g of hydroxyethyl methacrylate was added to the reaction mixture over a course of one minute, where after the temperature of the reaction mixture was maintained at 50° C. (while stirring) for approximately 3 hours. Then, the reaction mixture was poured into a container and allowed to cool to ambient temperature, as a urethane acrylate. The urethane acrylate was then coated onto a substrate and UV-cured using one of the methods described below. After which, various physical properties of the UV cured coating were tested using several of the testing procedures outlined below.

Example 16

Initially, 46.4 g dPET from Example E and 17 g Piothane® S-500 (a natural oil based polyol from Panolam Industries International, Inc., (Shelton, Conn.)) were added into the reaction vessel. In a separate container, 80 g tetrahydrofurfuryl acrylate (Sartomer® SR285 from Sartomer Company (Exton, Pa.)) and 0.16 g phenothiazine were premixed to form a homogeneous solution. Once the phenothiazine was fully dissolved in the tetrahydrofurfuryl acrylate, the solution was added to the reaction vessel forming a reaction mixture. The reaction mixture was then heated to approximately 50° C. and agitated once the mixture softened eventually forming a homogeneous mixture. The reaction mixture was then removed from heat source and allowed to cool to 25° C. while adding isophorone diisocyanate (125 g) drop wise over the course of approximately 2 minutes making sure the reactor contents did not exceed 65° C. Once the temperature stabilized around 25° C., 0.6 g dibutyltin dilaurate catalyst was added to the reaction mixture. Thereafter, once the temperature again stabilized, the reaction mixture was heated to a target temperature of 50° C. and allowed to remain at 50° C. while stirring for approximately one hour. Thereafter, 67.25 g of pentaerythritol triacrylate was added to the reaction mixture over a course of one minute, where after the temperature of the reaction mixture was maintained at 50° C. (while stirring) for approximately 3 hours. Afterwards, 66.66 g of hydroxyethyl methacrylate as added and allowed to react for an additional 1.5 hours. Then, the reaction mixture was poured into a container and allowed to cool to ambient temperature, as a urethane acrylate. The urethane acrylate was then coated onto a substrate and UV-cured using one of the methods described below. After which, various physical properties of the UV cured coating were tested using several of the testing procedures outlined below.

Example 17

Initially, 46.4 g dPET from Example E and 17 g Piothane® S-500 (a natural oil based polyol from Panolam Industries International, Inc., (Shelton, Conn.)) were added into the reaction vessel. In a separate container, 80 g tetrahydrofurfuryl acrylate (Sartomer® SR285 from Sartomer Company (Exton, Pa.)) and 0.16 g phenothiazine were premixed to form a homogeneous solution. Once the phenothiazine was fully dissolved in the tetrahydrofurfuryl acrylate, the solution was added to the reaction vessel forming a reaction mixture. The reaction mixture was then heated to approximately 50° C. and agitated once the mixture softened eventually forming a homogeneous mixture. The reaction mixture was then removed from heat source and allowed to cool to 25° C. while adding isophorone diisocyanate (125 g) drop wise over the course of approximately 2 minutes making sure the reactor contents did not exceed 65° C. Once the temperature stabilized around 25° C., 0.6 g dibutyltin dilaurate catalyst was added to the reaction mixture. Thereafter, once the temperature again stabilized, the reaction mixture was heated to a target temperature of 50° C. and allowed to remain at 50° C. while stirring for approximately one hour. Thereafter, 67.25 g of pentaerythritol triacrylate was added to the reaction mixture over a course of one minute, where after the temperature of the reaction mixture was maintained at 50° C. (while stirring) for approximately 3 hours. Afterwards, 59.48 g of hydroxyethyl acrylate as added and allowed to react for an additional 1.5 hours. Then, the reaction mixture was poured into a container and allowed to cool to ambient temperature, as a urethane acrylate. The urethane acrylate was then coated onto a substrate and UV-cured using one of the methods described below. After which, various physical properties of the UV cured coating were tested using several of the testing procedures outlined below.

Example 18

Initially, 46.4 g dPET from Example E and 17 g Piothane® S-500 (a natural oil based polyol from Panolam Industries International, Inc., (Shelton, Conn.)) were added into the reaction vessel. In a separate container, 80 g tetrahydrofurfuryl acrylate (Sartomer® SR285 from Sartomer Company (Exton, Pa.)) and 0.16 g phenothiazine were premixed to form a homogeneous solution. Once the phenothiazine was fully dissolved in the tetrahydrofurfuryl acrylate, the solution was added to the reaction vessel forming a reaction mixture. The reaction mixture was then heated to approximately 50° C. and agitated once the mixture softened eventually forming a homogeneous mixture. The reaction mixture was then removed from heat source and allowed to cool to 25° C. while adding hexamethylene diisocyanate (94.58 g) drop wise over the course of approximately 2 minutes making sure the reactor contents did not exceed 65° C. Once the temperature stabilized around 25° C., 0.6 g dibutyltin dilaurate catalyst was added to the reaction mixture. Thereafter, once the temperature again stabilized, the reaction mixture was heated to a target temperature of 50° C. and allowed to remain at 50° C. while stirring for approximately one hour. Thereafter, 67.25 g of pentaerythritol triacrylate was added to the reaction mixture over a course of one minute, where after the temperature of the reaction mixture was maintained at 50° C. (while stirring) for approximately 3 hours. Afterwards, 66.66 g of hydroxyethyl methacrylate as added and allowed to react for an additional 1.5 hours. Then, the reaction mixture was poured into a container and allowed to cool to ambient temperature, as a urethane acrylate. The urethane acrylate was then coated onto a substrate and UV-cured using one of the methods described below. After which, various physical properties of the UV cured coating were tested using several of the testing procedures outlined below.

Preparation of UV-Curable Coatings of Polyurethane Dispersions and Polyurethane Acrylates:

Two methods were used to prepare UV-cured urethane acrylate coatings. The first method used the urethane acrylates disclosed in Examples 11 and 12, wherein 2 wt % Darocur® 1173 photoinitiator (Ciba®, now part of BASF, (Ludwigshafen, Germany)) was individually added to Examples 11 and 12 and mixed thoroughly. Thereafter, the photoinitiator-containing urethane acrylates were coated onto either a glass, aluminum, or wood substrate wherein the initial "wet" coating was between 5 to 10 mil in thickness. Once applied to the substrate, the urethane acrylate coated substrate was allowed to reside uncovered at ambient conditions for about 30 minutes before being placed into an oven at 50° C. for about 30 minutes. After removing the urethane acrylate coated substrate from the oven, it was then exposed to sufficient UV light to initiate the polymerization of the acrylate materials by using a Heraeus Noble Light Fusion UV unit equipped with an LC6B benchtop conveyor set at 4 ft/min. and a 558432 H+ bulb. The UV-cured coatings had thicknesses of 1 to 2 mil which were thereafter tested using several of the procedures outlined below.

The second method used the urethane acrylates disclosed in Examples 13, and 17-18 to produce UV-cured urethane acrylate coatings, wherein Examples 13, 17, and 18 were individually mixed with 30 wt % tetrahydrofurfuryl acrylate (Sartomer® SR285 from Sartomer Company (Exton, Pa.)), 25 wt % methyl ethyl ketone, and 2 wt % Darocur® 1173 photoinitiator (Ciba®, now part of BASF, (Ludwigshafen, Germany)) and cast into 5 mil "wet" films on either a glass, aluminum, or wood substrate using a #50 wire-wound rod. The resulting films were flash evaporated under ambient conditions for 30 minutes and then placed in a 50° C. oven for 4 minutes. The cast films were then exposed to ultraviolet light using a Heraeus Noblelight Fusion UV unit equipped with an LC6B benchtop conveyor and a 558432 H+ bulb at a conveyor speed of 4 ft/min. The UV-cured coating had a thickness of approximately 2 mil on each of the glass, aluminum, and wood substrates which were thereafter tested using several of the procedures outlined below.

The main difference between the two methods of preparing a UV-cured urethane acrylate coating is that the second method added a solvent (methyl ethyl ketone) and an additional amount of tetrahydrofurfuryl acrylate in order to decrease the viscosity of the uncured urethane acrylate. Decreasing the viscosity using the MEK solvent and additional tetrahydrofurfuryl acrylate made it easier to apply the urethane acrylate to a substrate without impacting the physical properties of the UV-cured coating.

Examples of Polyethylene Terephthalate Acrylates:

The apparatus for Examples 19 to 22 directed to the preparation of polyethylene terephthalate acrylates from polyethylene terephthalate polyols consisted of (i) a 4 neck, 500 mL reaction vessel with a mechanical stirrer, (ii) a condenser, (iii) a thermocouple, (iv) a heating mantel, and (v) a dropping funnel.

Example 19

75 g dPET from Example A, 300 mL of tetrahydrofuran, 0.19 g phenothiazine, and 50.12 g triethylamine were added into the reaction vessel described above. The mixture was heated to 50° C. to dissolve the dPET ("polyol") in the tetrahydrofuran. The dissolved dPET solution (which appeared to be an opaque, grey solution) was then cooled to about 10° C. prior to adding 44.83 g acryloyl chloride drop wise over the course of 2 hours and then being stirred for another hour. The resulting product (which appeared to be an opaque pale amber solution with precipitated tryiethylamine hydrochloride salt) was vacuum filtered over a sufficient amount of Celite® 545 (Sigmam Aldrich, St. Louis, Mo.), stripped of solvent under vacuum, and then re-dissolved in 350 mL of methylene chloride. The methylene chloride solution was then washed with 10 wt % sodium hydroxide solution, then with 10 wt % sodium chloride solution, and then dried over anhydrous magnesium sulfate. The solvent was thoroughly stripped under vacuum at between about 40 to about 60° C. at 70 torr. The final polyethylene terephthalate acrylate product was medium amber/grey and opaque in appearance with a very low viscosity and a strong acrylate smell.

3 g of the polyethylene terephthalate acrylate product was mixed with 0.06 g Irgacure® 2959 photoinitiator (Ciba®, now part of BASF, Ludwigshafen, Germany) to form a UV curable polyethylene terephthalate acrylate composition. The UV curable polyethylene terephthalate acrylate was then coated as a 5 mil cast on an aluminum substrate using a #50 wire-wound rod and UV-cured using the method described below. After which, various physical properties of the UV cured coating were tested using several of the testing procedures outlined below.

Example 20

3 g of the polyethylene terephthalate acrylate product described above in Example 19 was mixed with 4.70 g tetrahydrofurfuryl acrylate and 0.06 g Irgacure® 2959 photoinitiator to form a UV curable polyethylene terephthalate acrylate composition. The UV curable polyethylene terephthalate acrylate was then coated as a 5 mil cast on an aluminum substrate using a #50 wire-wound rod and UV-cured using the method described below. After which, various physical properties of the UV cured coating were tested using several of the testing procedures outlined below.

Example 21

3 g of the polyethylene terephthalate acrylate product described above in Example 19 was mixed with 0.8 g tetrahydrofurfuryl acrylate, 6.5 g of the urethane acrylate in Example 1, and 0.20 g Irgacure® 2959 photoinitiator to form a UV curable polyethylene terephthalate acrylate and urethane acrylate composition. The UV curable polyethylene terephthalate acrylate and urethane acrylate composition was then coated as a 5 mil cast on an aluminum substrate using a #50 wire-wound rod and UV-cured using the method described below. After which, various physical properties of the UV cured coating were tested using several of the testing procedures outlined below.

Example 22

3 g of the polyethylene terephthalate acrylate product described above in Example 19 was mixed with 0.30 g glycol ether EB, 0.03 g of BYK® 028 (a silicone-containing defoamer from Altana, Wesel, Germany), and 0.06 g Irgacure® 2959 photoinitiator to form a UV curable polyethylene terephthalate acrylate composition. The UV curable polyethylene terephthalate acrylate composition was then coated as a 5 mil cast on an aluminum substrate using a #50 wire-wound rod and UV-cured using the method described below. After which, various physical properties of the UV cured coating were tested using several of the testing procedures outlined below.

Preparation of UV-Cured Polyethylene Terephthalate Acrylate Coatings:

As described above, the polyethylene terephthalate acrylates in Examples 19-22 were individually cast as 5 mil films on separate aluminum substrates using a #50 wire-wound rod. The resulting films were flash evaporated under ambient conditions for 30 minutes, then placed in an oven at 50° C. for 4 minutes. The films were then exposed to ultraviolet light using a Heraeus Noblelight Fusion UV unit equipped with an LC6B benchtop conveyor and a 558432 H+ bulb at a conveyor speed of 4 ft/min. The UV-cured coating had a thickness of approximately 2 mil on aluminum substrates which were thereafter tested using several of the procedures outlined below.

Testing Procedures

For the applicable testing procedures, the PUDs of Examples 1-10 were diluted with water to 25-35% nonvolatiles (unless the PUDs were prepared at lower concentrations). The 35% solutions and their associated films were used for measuring pH, viscosity, pencil hardness, water soak, spot test, and MEK double rubs. Film properties were determined on metal plates on which up to 10 mil (wet thickness) films were cast from the PUDs of Examples 1-10. Additionally, films produced from the UV cured urethane acrylates of Examples 11-18 and the UV cured polyethylene terephthalate acrylates of Examples 19-22 were about 1 to 2 mil in thickness.

pH Measurements

The pH of the polyurethane dispersions in Examples 1-10 and the UV curable polyurethane dispersion in Example 11 were measured using a pH meter calibrated at pH 2 to 12. The results are presented in Tables 1 and 3, respectively.

Viscosity

The viscosity of the polyurethane dispersions in Examples 1-10 and the UV curable polyurethane dispersion in Example 11 were measured using a viscometer. The #31 spindle was used for most samples. PUDs were equilibrated in a 25° C. water bath for 1 h before measurements were recorded. The results are in Tables 1 and 3, respectively.

Pencil Hardness

Pencil hardness was tested using the methods outlined by ASTM D3363, which covers a procedure for the rapid determination of film hardness of an organic coating on a substrate in terms of drawing leads or pencil leads of known hardness using the scale presented below.

Softer-6B-5B-4B-3B-2B-B-HB-F-H-2H-3H-4H-5H-6H-7H-8H-9H-Harder

The test was performed by pushing the tip of a pencil across a coated surface at a 45 degree angle. The process is started with a soft lead and continued up the scale of hardness until the pencil cuts into the film. The last pencil grade, which did not cut the film, is reported.

Water Soak

A film-coated panel was placed into a heated, temperature controlled bath. For Examples 11 and 12, the bath was kept at 38° C. for 3 hours. For Examples 13-18, the bath was kept at 100° C. for 3 hours. Each test panel was then removed and the performance was measured using the following scale: (i) "4F" was noted for coatings that were completely dissolved in the water bath and nothing remained attached to the panel, (ii) "3F" was noted for coatings that were delaminated and severely damaged but not dissolved in the water bath, (iii) "2F" was noted for coatings that showed significant blistering, discoloration, and initial signs of delamination, (iv) "1F" was noted for coatings that showed very minor signs of damage, blistering, and discoloration, and (v) "0F" was noted for coatings showing no signs of damage or evidence that the film-coated panel was placed in the heated water bath.

Spot/Stain Tests

Fully saturated cotton balls with media to be tested (e.g., MEK, hot coffee, etc.) are placed inside of a cap which is then placed on the test film so that the cotton ball is in direct contact with the film. The cap and cotton ball were removed after a set amount of time (1 hour or 24 hours, as defined in the test results below). Any excess of the testing media was removed and then the test film was analyzed based on the following scale: A "5" corresponds to no damage to the film and no evidence a staining substance was ever placed on the coating; a "4" corresponds to the coating showing very minor signs of damage but the stain did not penetrate through to the substrate; a "3" corresponds to the coating beginning to show some degradation, blistering, and/or coloration, a "2" corresponds to the coatings still being intact but severely damaged, possibly to the point of complete delamination; a "1" corresponds to the coating being completely destroyed and/or dissolved by the staining substance.

MEK Double Rub

This test was performed using the methods presented in ASTM D4752, which describes a solvent rub technique for assessing the methyl ethyl ketone (MEK) resistance of the films. The test was performed by soaking a pad of cheese cloth with MEK, placing a protected index finger into the pad while holding the excess cloth with the thumb and remaining fingers of the same hand. The index finger was held at a 45 degree angle to the film surface, pushed away from and then pulled towards the analyst. One forward and backward motion constituted a double rub. The rubs were continued and solvent replenished as needed until the surface of the test panel was exposed.

Color Test

Color was assessed using the Gardner Color scale as set out in ASTM D1544-04, wherein the color of transparent liquids was measured by comparing the liquids to glass standards numbered 1 to 18, wherein 1 corresponds to colorless clear and 18 corresponds to dark clear.

Konig (Pendulum) Hardness Test

For select samples of the UV cured urethane acrylate coatings, the Konig (Pendulum) Hardness test as set out in ASTM D4366-95 was used to measure hardness before and after the UV curing. The Konig (Pendulum) Hardness test is based on the fact that the amplitude of oscillations of a pendulum resting on a sample decreases more rapidly the softer the films. The time in seconds (damping time) for the pendulum deflection to slow down to a specific value is taken as the hardness of the coating.

Mandrel Bend Test

For select samples of the UV cured urethane acrylate coatings and polyethylene terephthalate acrylate coatings, the Mandrel Bend test was used to test their ability to resist cracking when elongated. The Mandrel Bend test encompassed the steps disclosed in ASTM D522-93a (2008). In essence, the Mandrel Bend test bends a coated metal sheet over a conical or cylindrical mandrel and cracks, color change, adhesion etc. of the coating are evaluated. Corresponding results, produced by decreasing mandrel sizes, indicate the degree of elasticity of the coating.

Taber Abrasion Test:

For select samples the Taber Abrasion test was used to determine the wear resistance of the coatings as set out in ASTM D4060-10. Test specimens disks are spun on a turntable and are abraded by a pair of abrading wheels for a specified number of cycles under a specified load. Abrasion resistance is reported as the change in mass of the test specimen or change in mass due to material loss from abrasion.

Cross Hatch Adhesion Test:

For selected samples of the UV cured urethane acrylate coatings and polyethylene terephthalate acrylate coatings, a Cross Hatch Adhesion test was used to determine the quality of adhesion of the coating to the substrate. The Cross Hatch Adhesion test encompassed the steps described in ASTM D3359-09e2 consisting of: (i) making a lattice pattern in the film with the appropriate tool, cutting to the substrate, (ii) brushing in diagonal directions 5 times each, using a brush pen or tape over the cut, and removing with Permacel™ tape (Nitto Denko Co., Pleasant Prairie, Wis.), and (iii) examining the grid area using an illuminated magnifier. A "5B" or "0" rating corresponds to a lattice pattern having smooth edges without any of the square of the lattice detached; a "4B" or "1" rating corresponds to detachment of small flakes of the coatings at the intersections of the cuts, wherein less than 5% of the cross-cut area is affected; a "3B" or "2" rating corresponds to a cross-cut area having an affected area greater than 5% but less than 15%, wherein the affected area has flaking along the edges or intersections of the cuts; a "2B" or "3" rating corresponds to a cross-cut area having an affected area greater than 15% but less than 35%, wherein the affected area has flaking along the edges or intersections of the cuts and parts or whole sections of squares in the lattice are flaking; a "1B" or a "4" rating corresponds to a cross-cut area having an affected area greater than 35% but less than 65%, wherein the affected area has flaking along the edges or intersections of the cuts and parts or whole sections of squares in the lattice are flaking; a "0B" or "5" rating corresponds to any degree of flaking that cannot be classified by the "1B" or "4" rating.

Test Results

The polyurethane dispersions in Examples 1-10 were subjected to the procedures set out above for measuring pH, viscosity, color, pencil hardness, water soak, and MEK double rub. In addition, the % solids of the polyurethane dispersions were calculated by measuring the final weight after drying in an elevated temperature oven divided by the total weight. The test results are presented in Table 4. The dashed line for some results should be interpreted as a measurement that was not taken rather than one that did not have measurable results.

TABLE 4

| Example # | pH | % Solids | Viscosity Measurements cP | Viscosity Measurements T (° C.) | Color (Gardner) | Pencil Hardness | Water Soak | MEK D.R. |
|---|---|---|---|---|---|---|---|---|
| 1 | 8.17 | 28.1 | 297 | 21 | 3 | 5H | 4F | — |
| 2 | 8.51 | 28.02 | 1670 | 21 | 3 | 8H | 1F | — |
| 3 | — | — | — | — | — | — | — | — |
| 4 | 4.51 | 28.0 | 420 | 22.4 | 4-5 | 4H | 2F | 30 |
| 5 | — | — | — | — | — | — | — | — |
| 6 | — | 27.4 | — | — | — | — | — | 40 |
| 7 | 8.2 | 27.8 | 523 | 22.1 | 4 | 8H | 2F | — |
| 8 | 4.75 | 27.5 | 499 | 25 | 4 | — | — | — |
| 9 | 8.2 | 27.5 | 209 | 25 | 4-5 | 7H | 3F | — |
| 10 | 8.65 | 31.2 | — | — | — | — | — | — |

The results in Table 1 suggest that the polyols presently disclosed and/or claimed herein and characterized in Table 3 can be used in the formation of a polyurethane coatings which have physical properties equal to, if not better, than other polyurethanes in the prior art. Such polyurethanes can be used for a variety of applications.

Additionally, dPETs A-F were analyzed by observing their colors and odors, and measuring the viscosity of the dPETs at 105° C. and at various RPMs and % torques. Additionally, the dPETs A-C and E-F were analyzed using GPC to determine the percentage of the various oligomers in the dPET compositions The OH number titration method set out in ASTMs E222 and D4274 were used to determine the mg KOH/g resin ("OH Number"). The acid number titration was also determined using the test methods set out in ASTMs E222 and D4274. The results of the above-referenced analysis are contained in Tables 5 and 6.

TABLE 5

| Example | Viscosity Measurements cP | Viscosity Measurements T (° C.) | Viscosity Measurements RPM | Viscosity Measurements % Torque | Acid Number | OH Number | Color | Odor |
|---|---|---|---|---|---|---|---|---|
| A | 997.8 | 105 | 15 | 50 | 13 | 365 | Light Grey | Sweet Glycol |
| B | 169.3 | 105 | 90 | 51 | 12 | 330 | Light Grey | Sweet Glycol |

TABLE 5-continued

| | Viscosity Measurements | | | | Acid | OH | | |
|---|---|---|---|---|---|---|---|---|
| Example | cP | T (° C.) | RPM | % Torque | Number | Number | Color | Odor |
| C | 44.6 | 105 | 250 | 37.2 | 16 | 480 | Light Grey | Sweet Glycol |
| D | 130 | 105 | 117 | 50.7 | 7.3 | 356 | Light Grey/Green | Sweet Solvent |
| E | 90.7 | 105 | 165 | 49.9 | 15 | 391 | Light Brown | Glycol/slight sesame oil |
| F | — | — | — | — | — | — | Dark Brown | Burnt sesame oil |

TABLE 6

| | GPC % Peak Area of UV Chromaphoe | | | | | |
|---|---|---|---|---|---|---|
| Example | 1 | 2 | 3 | 4 | 5 | 6+ |
| A | 29.5% | 27.7% | 19.0% | 11.5% | 6.1% | 6.2% |
| B | 27.1% | 27.7% | 19.8% | 11.8% | 6.7% | 7.0% |
| C | 39.2% | 30.0% | 16.7% | 8.2% | 3.5% | 2.4% |
| D | — | — | — | — | — | — |

TABLE 6-continued

| | GPC % Peak Area of UV Chromaphoe | | | | | |
|---|---|---|---|---|---|---|
| Example | 1 | 2 | 3 | 4 | 5 | 6+ |
| E | 30.0% | 28.1% | 18.8% | 11.2% | 6.1% | 5.8% |
| F | 24.0% | 25.2% | 19.2% | 13.1% | 7.6% | 10.8% |

Table 5 illustrates that the industrial scale-like process that included the removal of byproducts produced a dPET (Example E) with similar properties to the dPETs produced in the lab at a bench scale that did not require the removal of byproducts. Table 5 also illustrates, by way of Example F, that the industrial scale-like process will not work correctly without pulling off the byproducts (as described above) during the reaction. The failure to pull of the byproducts in Example F resulted in a dark, viscous material that did not represent an oligomeric mixture of polyethylene terephthalate.

Table 6 illustrates that dPETs A-F have unique oligomeric profiles ("1" corresponds to monomer, "2" to dimer, etc.), which contribute to the physical properties associated with the various polyurethane dispersions, polyurethanes, urethane acrylates, and polyethylene terephthalate acrylates that can be formed using such dPETs as presently disclosed and/or claimed herein.

The urethane acrylates in several of Examples 11-18 and their respective UV cured coatings were subjected to several of the procedures set out above including the procedures for measuring pH, viscosity, pencil hardness, water soak, Konig (Pendulum) Hardness (before UV and after UV), cross hatch adhesion, the 1" Mandrel bend test, and MEK double rub. Not all of the urethane acrylate examples were tested using each available test procedure. As such, unless otherwise indicated, the dashes in Tables 7 and 8 below should be interpreted as if the measurement was not taken, rather than a sample that did not have measureable results. Additionally, all of the test measurement included in Tables 7 and 8 were taken on films after the urethane acrylate had been UV cured with the exception of the pH of Example 11 and the Konig Hardness test (before UV) measurements.

TABLE 7

| Example | pH | Dry Film Thickness (mil) | Viscosity cP; T (21° C.) | Color | MEK D.R. | Pencil Hardness | Konig Hardness (before UV) | Konig Hardness (after UV) |
|---|---|---|---|---|---|---|---|---|
| 11 | 7.6 | — | 150 | White | >200 | — | 22-41 | 137-146 |
| 12 | — | — | — | white | >200 | 5H | — | — |
| 13 | — | 2.14 | — | — | >200 | 6H | — | 144.3 |
| 17 | — | 1.8 | — | — | >200 | 6H | — | 145.3 |
| 18 | — | 1.97 | — | — | >200 | 6H | — | 85.7 |

TABLE 8

| Example | Water Soak | Taber Abrasion (mg loss/ 1000 cycles) | Cross Hatch Adhesion Aluminum | Cross Hatch Adhesion Maple Wood | Cross Hatch Adhesion Oak Wood | 1" Mandrel Bend |
|---|---|---|---|---|---|---|
| 11 | — | — | — | — | — | — |
| 12 | 3F | — | — | — | — | — |
| 13 | 0F | 36.5 | 0 | 1.0 | 1.3 | F |
| 17 | 0F | 29 | 0 | 1.3 | 1.7 | F |
| 18 | 0F | 30.2 | 0 | 3.7 | 4.7 | F |

UV cured coatings of the urethane acrylates in several of Examples 11-18 were also subject to the stain/spot test (as described above) for numerous different solvents and compositions on a urethane acrylate coated wood substrate. The letter "A" next to the rating signifies that the solvent or composition was left on the coated wood substrate for only 1 hour, while the letter "B" next to the rating signifies that the solvent or composition was left on the coated wood substrate for approximately 24 hours. As described above, a "5" corresponds to no damage to the film and no evidence a staining substance was ever placed on the coating; a "4" corresponds to the coating showing very minor signs of damage but the stain did not penetrate through to the substrate; a "3" corresponds to the coating beginning to show some degradation, blistering, and/or coloration, a "2" corresponds to the coatings still being intact but severely damaged, possibly to the point of complete delamination; a "1" corresponds to the coating being completely destroyed and/or dissolved by the staining substance. The results are presented below in Table 9.

TABLE 9

| Solvent or Composition | Example 11 | Example 12 | Example 13 | Example 17 | Example 18 |
|---|---|---|---|---|---|
| MEK | 5A | 2A | 5A | 5A | 5A |
| IPA | 5A | 4A | 5A | 5A | 5A |
| Mustard | 5A | — | 5A | 5A | 5A |
| Vinegar | 4-5B | 4B | 5B | 5B | 5B |
| Lemon Juice | 5B | — | 5B | 5B | 5B |
| Orange Juice | 5B | — | 5B | 5B | 5B |
| Grape Juice | 5B | — | 5B | 5B | 5B |
| Catsup | 5B | — | 5B | 5B | 5B |
| Olive oil | 5B | — | 5B | 5B | 5B |
| Alcohol | 4-5B | — | 5B | 5B | 5B |
| Windex ® (S. C. Johnson, Racine, WI) | 5B | 4B | 5B | 5B | 5B |
| Water | 5B | 4B | 5B | 5B | 5B |
| Cyclohexane | — | 5A | 5B | 5B | 5B |
| Hot Coffee | 5B | — | 5B | 5B | 5B |
| Perspiration | 5B | — | 5B | 5B | 5B |
| 1% Detergent | 5B | — | 5B | 5B | 5B |

The results in Table 9 indicate that the UV cured urethane acrylate coatings as described and/or claimed herein have excellent stain resistant properties.

UV cured coatings of the polyethylene terephthalate acrylates in Examples 19-22 were subjected to several of the procedures set out above including the procedures for measuring pencil hardness, cross hatch adhesion, MEK double rub, the 1" and ⅛" Mandrel bend tests, and water soak and pencil hardness after water soak.

TABLE 10

| Example # | Dry Film Thickness (mil) | Pencil Hardness | Cross Hatch Adhesion | MEK D.R. | Mandrel Bend 1" | Mandrel Bend ⅛" | Water Soak | Pencil Hardness after Water Soak |
|---|---|---|---|---|---|---|---|---|
| 19 | 1.11 | >9H | 1B | >200 | F | F | 0F | >H |
| 20 | 0.72 | 5H | 5B | 120 | P | P | 1F | <H |
| 21 | 2.64 | >9H | 1.3B | >200 | F | F | 0F | >H |
| 22 | 1.59 | >9H | 4B | >200 | F | F | 0F | >H |

What is claimed is:

1. A radiation-curable composition comprising:
  (i) at least one hydroxy-functional polyethylene terephthalate oligomer consisting of recurring units from polyethylene terephthalate and a glycol selected from the group consisting of ethylene glycol, propylene glycol, diethylene glycol, neopentyl glycol, recycled versions thereof, and mixtures thereof; and
  (ii) an ethylenically unsaturated photopolymerizable compound.

2. The composition of claim 1 comprising:
  the photopolymerizable compound and
  a polyurethane resin comprising a reaction product formed by reacting the polyethylene terephthalate oligomer with a polyisocyanate.

3. The composition of claim 2 wherein the polyurethane resin comprises a reaction product of the polyisocyanate, the polyethylene terephthalate oligomer, and at least one water solubilizing monomer.

4. The composition of claim 3 further comprising water.

5. The composition of claim 1 further comprising a photoinitiator.

6. The composition of claim 2 wherein the polyisocyanate is selected from the group consisting of isophorone diisocyanate (IPDI), methylene bisphenyl isocyanate (MDI), dicyclohexylmethane 4,4'-diisocyanate (H12MDI), cyclohexyl diisocyanate (CHDI), m-tetramethylxylylene diisocyanate (m-TMXDI), tetramethylxylylene diisocyanate (TMXDI), ethylene diisocyanate, 1,2-diisocyanatopropane, 1,3-diisocyanatopropane, 1,4-diisocyanatobutane, 1,5-diisocyanatopentane, hexamethylene diisocyanate (HDI), lysine diisocyanate, 1,4-methylene bis-(cyclohexyl isocyanate), toluene diisocyanate (TDI), m-xylylenediisocyanate (MXDI), p-xylylenediisocyanate, 4-chloro-1,3-phenylene diisocyanate, 1,5-tetrahydro-naphthalene diisocyanate, 4,4'-dibenzyl diisocyanate, 1,2,4-benzene triisocyanate, xylylene diisocyanate (XDI), 1,6-diisocyanatohexane, 2-methyl-1,5-diisocyanatopentane, 1,5-diisocyanato-2,2-dimethylpentane, 2,2,4-trimethyl-1,6-diisocyanatohexane, 2,4,4-trimethyl-1,6-diisocyanatohexane, 1,10-diisocyanato-decane, 1,3-diisocyanatocyclohexane, 1,4-diisocyanatocyclohexane, 1,3-bis-(isocyanatomethyl)cyclohexane, 1,4-bis-(isocyanatomethyl)cyclohexane, isophorone diisocyanate, 4,4'-diisocyanatodicyclohexylmethane, triisocyanatononane, diisocyanato-1,3-dimethylcyclohexane, 1-isocyanato-1-methyl-3-isocyanatomethylcyclohexane, 1-isocyanato-1-methyl-4-isocyanatomethylcyclohexane, bis-(isocyanatomethyl)-norbornane, 1,5-naphthalene diisocyanate, 1,3-bis-(2-isocyanatoprop-2-yl)benzene, 1,4-bis-(2-isocyanatoprop-2-yl)benzene, 2,4-diisocyanatotoluene, 2,6-diisocyanatotoluene, 2,4'-diisocyanatodiphenylmethane, 4,4'-diisocyanatodiphenylmethane, 1,5-diisocyanatonaphthalene, 1,3-bis(isocyanatomethyl)benzene, and combinations thereof.

7. The composition of claim 6 wherein the polyisocyanate is selected from the group consisting of toluene diisocyanate, isophorone diisocyanate, hexamethylene diisocyanate, and combinations thereof.

8. The composition of claim 1 wherein the ethylenically unsaturated photopolymerizable compound is selected from the group consisting of butanediol diacrylate, 1,6-hexanediol diacrylate, tripropylene glycol diacrylate, diethylene glycol diacrylate, triethylene glycol diacrylate, tetraethylene glycol diacrylate, N-vinyl pyrrolidone, neopentyl glycol diacrylate, isobornyl acrylate, 2-ethylhexyl acrylate, methyl methacrylate, ethyl methacrylate, 2-ethylhexyl methacrylate, isobutyl methacrylate, glycidyl methacrylate, glycidyl acrylate, butyl acrylate, 2-hydroxyethyl (meth)acrylate, 2-methoxyethyl acrylate, 2-phenoxyethyl acrylate, 2-hydroxypropyl acrylate, benzyl acrylate, tetrahydrofurfuryl acrylate, pentaerythritol triacrylate and combinations thereof.

9. The composition of claim 1 further comprising an additional polyol selected from the group consisting of polyether polyols, aliphatic polyester polyols, polycarbonate polyols, aromatic polyester polyols, polyester/ether polyols, and $C_3$ to $C_{18}$ glycols containing 2 to 8 hydroxyl groups.

10. An article of manufacture comprising the composition of claim 1.

11. An article of manufacture comprising the composition of claim 2.

12. A film comprising the composition of claim 1.

13. A film comprising the composition of claim 2.

* * * * *